US011918399B2

(12) United States Patent
Konno et al.

(10) Patent No.: US 11,918,399 B2
(45) Date of Patent: Mar. 5, 2024

(54) CONTROL DEVICE, CONTROL METHOD, AND CONTROL PROGRAM

(71) Applicant: FUJIFILM CORPORATION, Tokyo (JP)

(72) Inventors: Shinichiro Konno, Kanagawa (JP); Yoshie Fujimoto, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 242 days.

(21) Appl. No.: 17/486,953

(22) Filed: Sep. 28, 2021

(65) Prior Publication Data
US 2022/0096031 A1 Mar. 31, 2022

(30) Foreign Application Priority Data
Sep. 30, 2020 (JP) .................................. 2020-166463

(51) Int. Cl.
*A61B 6/00* (2006.01)
*A61B 6/04* (2006.01)
(Continued)

(52) U.S. Cl.
CPC ............ *A61B 6/502* (2013.01); *A61B 6/0414* (2013.01); *A61B 6/542* (2013.01);
(Continued)

(58) Field of Classification Search
CPC .. A61B 6/00; A61B 6/04; A61B 6/502; A61B 6/542; A61B 6/0414; A61B 6/0492;
(Continued)

(56) References Cited

U.S. PATENT DOCUMENTS 7,732,775 B2 * 6/2010 Kashiwagi ........... A61B 6/0414
250/363.05
2009/0299218 A1 12/2009 Holler et al.
(Continued)

FOREIGN PATENT DOCUMENTS

JP 2007-236805 A 9/2007
JP 2008-086389 A 4/2008
(Continued)

OTHER PUBLICATIONS

English language translation of the following: Office action dated Apr. 18, 2023 from the JPO in a Japanese patent application No. 2020-166463 corresponding to the instant patent application. This office action translation is submitted now in order to supplement the understanding of the cited references which are being disclosed in the instant Information Disclosure Statement.

*Primary Examiner* — Jurie Yun
(74) *Attorney, Agent, or Firm* — SOLARIS Intellectual Property Group, PLLC

(57) ABSTRACT

A control device including: at least one processor, wherein the processor is configured control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field are switched.

20 Claims, 19 Drawing Sheets

(51) Int. Cl.
*G03B 21/20* (2006.01)
*G06T 7/00* (2017.01)

(52) U.S. Cl.
CPC ........ *G03B 21/2053* (2013.01); *G06T 7/0012* (2013.01); *G06T 2207/30068* (2013.01)

(58) Field of Classification Search
CPC .... A61B 6/06; A61B 6/54; G06T 7/00; G06T 7/0012; G06T 2207/30068; G03B 21/20; G03B 21/2053; G03B 42/02
See application file for complete search history.

(56) References Cited

U.S. PATENT DOCUMENTS

| | | |
|---|---|---|
| 2014/0328458 A1 | 11/2014 | Erhard et al. |
| 2017/0172531 A1 | 6/2017 | Sugiyama et al. |
| 2020/0253572 A1 | 8/2020 | Nakayama |

FOREIGN PATENT DOCUMENTS

| | | |
|---|---|---|
| JP | 2009-285345 A | 12/2009 |
| JP | 2014-533548 A | 12/2014 |
| JP | 2017-113540 A | 6/2017 |
| JP | 2020-127650 A | 8/2020 |
| WO | 2020/069031 A1 | 4/2020 |

\* cited by examiner

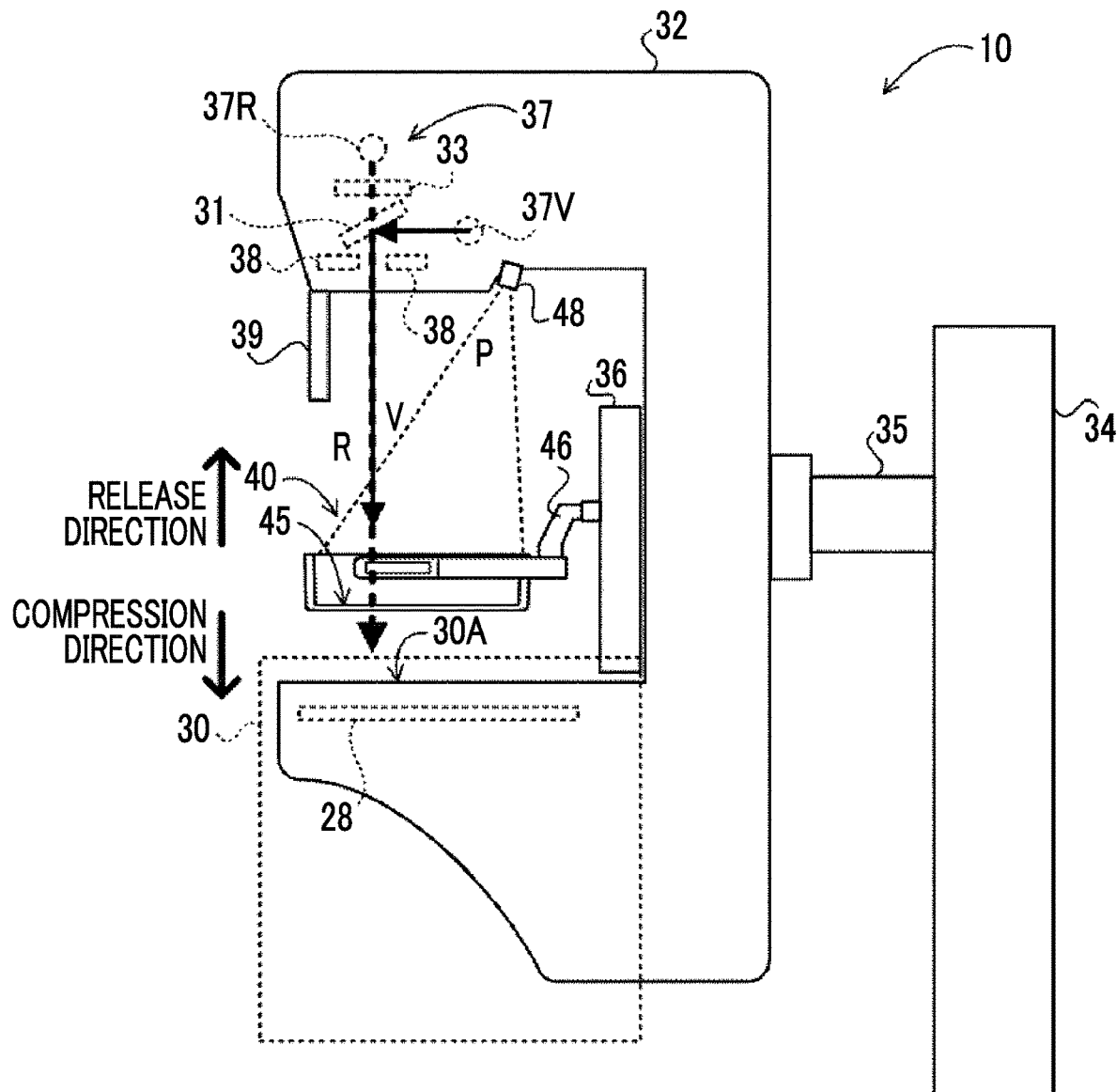

CONTROL DEVICE, CONTROL METHOD, AND CONTROL PROGRAM

CROSS-REFERENCE TO RELATED APPLICATION

The present application claims priority under 35 U.S.C. § 119 to Japanese Patent Application No. 2020-166463 filed on Sep. 30, 2020. The above application is hereby expressly incorporated by reference, in its entirety, into the present application.

BACKGROUND

Technical Field

The present disclosure relates to a control device, a control method, and a non-transitory computer-readable storage medium storing a control program.

Description of the Related Art

A mammography apparatus is known which irradiates a breast compressed by a compression member with radiation to capture a radiographic image. In a case in which a projection image is projected to perform imaging, information or the like for assisting the imaging may be displayed. For example, JP2008-086389A discloses a technique that displays a skin line of the breast on a liquid crystal display (LCD) and displays a projection image thereof on a projection surface of a compression member.

Further, in the mammography apparatus, there is known a technique which emits visible light to project the range of the irradiation field, thereby indicating the range of the irradiation field of radiation. For example, JP2008-086389A discloses a technique which indicates the irradiation field of radiation using visible light emitted from a projection light source.

Light is emitted for both the projection of a projection image and the projection of the irradiation field. Therefore, in a case in which the projection image and the irradiation field are projected at the same time, light overlaps. As a result, in some cases, the projection image and the irradiation field are unrecognizable. For example, in a case in which visible light for projecting the range of the irradiation field is emitted while the projection image is being projected, display corresponding to the projection image may not be visible due to the emitted visible light.

The present disclosure has been made in view of the above-mentioned problems, and an object of the present disclosure is to provide a control device, a control method, and a non-transitory computer-readable storage medium storing a control program that can prevent a projection image and a range of an irradiation field from being unrecognizable.

SUMMARY

In order to achieve the above object, according to a first aspect of the present disclosure, there is provided a control device comprising at least one processor. The processor is configured to control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field are switched.

According to a second aspect of the present disclosure, in the control device according to the first aspect, the processor may perform the control in a case in which an instruction to start the projection of the range of the irradiation field is received while the projection image is being projected and may perform the control in a case in which an instruction to end the projection of the range of the irradiation field is received.

According to a third aspect of the present disclosure, in the control device according to the first aspect, the processor may display the range of the irradiation field using the projection image in a case in which the projection image is projected.

According to a fourth aspect of the present disclosure, in the control device according to the third aspect, the processor may make at least one of brightness or saturation of a region of the projection image within the range of the irradiation field different from the at least one of the brightness or the saturation of a region outside the range of the irradiation field to display the range of the irradiation field.

According to a fifth aspect of the present disclosure, in the control device according to the third aspect, the processor may display the range of the irradiation field in the projection image using a line or a mark indicating a boundary between an inside and an outside of the irradiation field.

According to a sixth aspect of the present disclosure, in the control device according to the first aspect, in a case in which an instruction to start the projection of the projection image and an instruction to start the projection of the range of the irradiation field are received, instead of the control, the processor may perform control to project both the range of the irradiation field and a projection image of which at least one of brightness or saturation is lower than that in a case in which only the projection image is projected.

According to a seventh aspect of the present disclosure, in the control device according to the first aspect, in a case in which an instruction to start the projection of the projection image and an instruction to start the projection of the range of the irradiation field are received, instead of the control, the processor may perform control to project both the projection image and a range of the irradiation field in which the visible light is dimmer than that in a case in which the range of the irradiation field is projected by the reception of only the instruction to start the projection of the range of the irradiation field of the instructions.

Further, in order to achieve the above object, according to an eighth aspect of the present disclosure, there is provided a control device comprising at least one processor. The processor is configured to control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that, in a case in which one of projection of the projection image and projection of the range of the irradiation field is performed and an instruction to start the other projection is received, the projection image or the range of the irradiation field corresponding to the other projection is displayed to be more highlighted than the projection image or the range of the irradiation field corresponding to the one projection.

According to a ninth aspect of the present disclosure, in the control device according to the eighth aspect, in a case in which the one projection is the projection of the projection image, the processor may decrease at least one of brightness or saturation of the projection image as the control.

According to a tenth aspect of the present disclosure, in the control device according to the eighth aspect, in a case in which the one projection is the projection of the projection image, the processor may brighten the visible light as the control.

According to an eleventh aspect of the present disclosure, in the control device according to the eighth aspect, in a case in which the one projection is the projection of the range of the irradiation field, the processor may dim the visible light as the control.

According to a twelfth aspect of the present disclosure, in the control device according to the eighth aspect, in a case in which the one projection is the projection of the range of the irradiation field, the processor may increase at least one of brightness or saturation of the projection image as the control.

Further, in order to achieve the above object, according to a thirteenth aspect of the present disclosure, there is provided a control device comprising at least one processor. The processor is configured to control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that the projection image to be projected is switched between a case in which the range of the irradiation field is displayed and a case in which the range of the irradiation field is not displayed.

According to a fourteenth aspect of the present disclosure, in the control device according to the thirteenth aspect, in a case in which the range of the irradiation field is displayed, the processor may perform control to switch to a projection image for displaying information outside the range of the irradiation field or control to switch a projection position of the projection image to a state in which information is displayed outside the range of the irradiation field.

In addition, in order to achieve the above object, according to a fifteenth aspect of the present disclosure, there is provided a control method comprising controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field are switched.

Further, in order to achieve the above object, according to a sixteenth aspect of the present disclosure, there is provided a control method comprising controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that, in a case in which one of projection of the projection image and projection of the range of the irradiation field is performed and an instruction to start the other projection is received, the projection image or the range of the irradiation field corresponding to the other projection is displayed to be more highlighted than the projection image or the range of the irradiation field corresponding to the one projection.

Furthermore, in order to achieve the above object, according to a seventeenth aspect of the present disclosure, there is provided a control method comprising controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that the projection image to be projected is switched between a case in which the range of the irradiation field is displayed and a case in which the range of the irradiation field is not displayed.

Moreover, in order to achieve the above object, according to an eighteenth aspect of the present disclosure, there is provided a non-transitory computer-readable storage medium storing a control program that causes a computer to perform a process comprising controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field are switched.

In addition, in order to achieve the above object, according to a nineteenth aspect of the present disclosure, there is provided a non-transitory computer-readable storage medium storing a control program that causes a computer to perform a process comprising controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that, in a case in which one of projection of the projection image and projection of the range of the irradiation field is performed and an instruction to start the other projection is received, the projection image or the range of the irradiation field corresponding to the other projection is displayed to be more highlighted than the projection image or the range of the irradiation field corresponding to the one projection.

Further, in order to achieve the above object, according to a twentieth aspect of the present disclosure, there is provided a non-transitory computer-readable storage medium storing a control program that causes a computer to perform a process comprising controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that the projection image to be projected is switched between a case in which the range of the irradiation field is displayed and a case in which the range of the irradiation field is not displayed.

According to the present disclosure, it is possible to prevent the projection image and the range of the irradiation field from being unrecognizable.

BRIEF DESCRIPTION OF THE DRAWINGS

Exemplary embodiments according to the technique of the present disclosure will be described in detail based on the following figures, wherein:

FIG. 2A is a side view illustrating an example of the outward appearance of a mammography apparatus according to the embodiment.

DETAILED DESCRIPTION

Hereinafter, embodiments of the present disclosure will be described in detail with reference to the drawings. In addition, each of the embodiments does not limit the present disclosure.

First Embodiment

Figure 1:
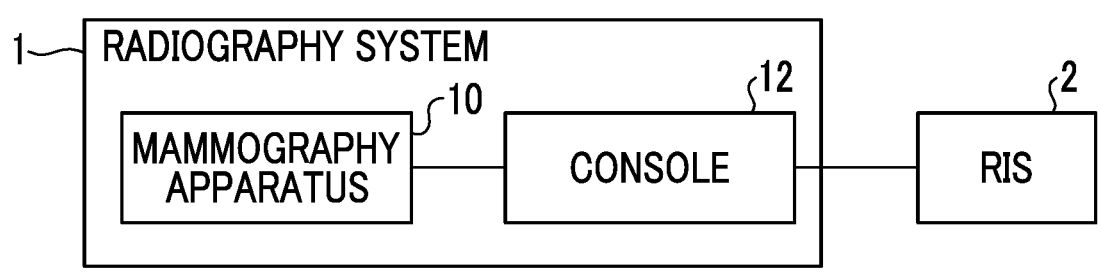
FIG. 1 is a schematic diagram illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of a control device according to the present disclosure.

Figure 2B:
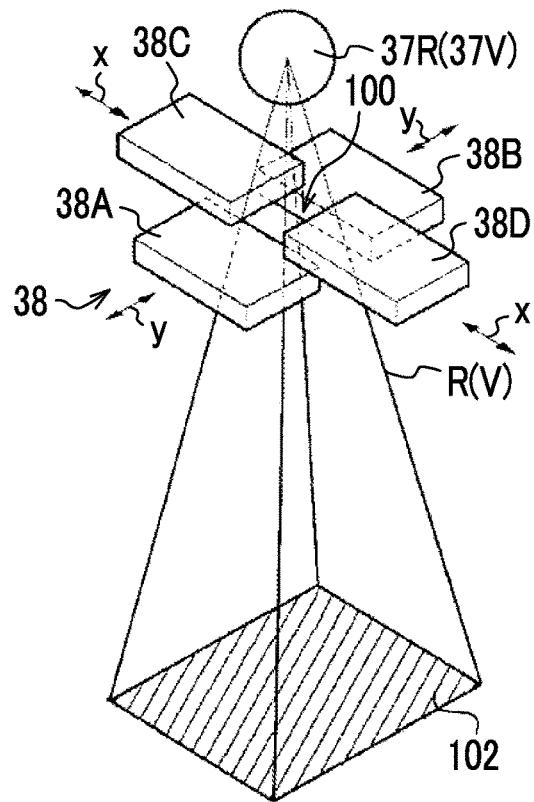
FIG. 2B is a perspective view illustrating an example of the configuration of a collimator according to the embodiment.
Figure 3:
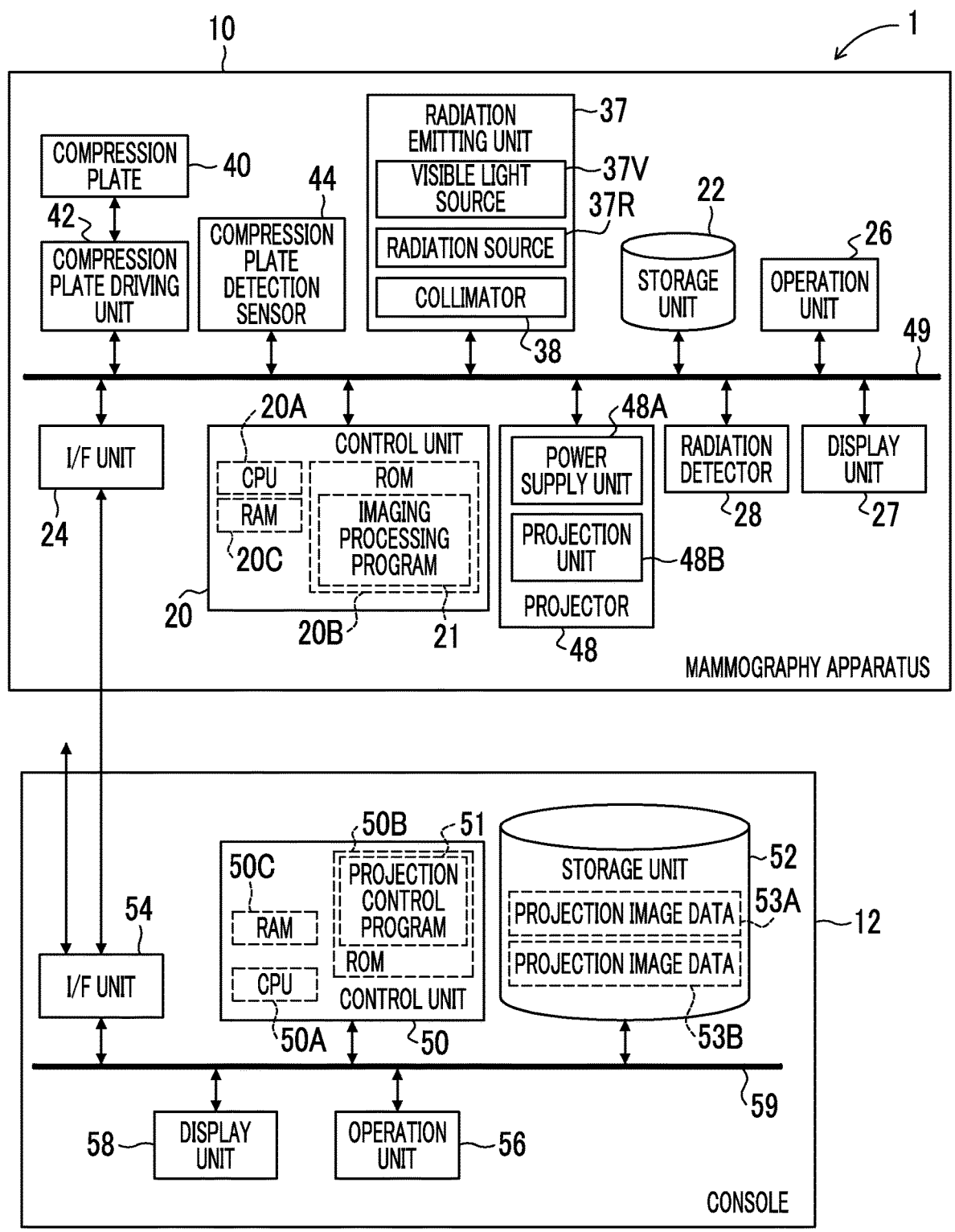
FIG. 3 is a block diagram illustrating an example of the configuration of the mammography apparatus and a console according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 3 is a functional block diagram illustrating an example of the configuration of the mammography apparatus 10 and the console 12 according to this embodiment.

The mammography apparatus 10 according to this embodiment irradiates a breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting, for example, on a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R, a visible light source 37V, and a collimator 38. As illustrated in FIG. 2A, the radiation emitting unit 37 is provided in an arm portion 32 together with the imaging table 30 and a compression unit 36. As illustrated in FIG. 2A, a face guard 39 is attachably and detachably provided at a position of the arm portion 32 which is close to the subject below the radiation emitting unit 37. The face guard 39 is a protective member for protecting the subject from the radiation R emitted from the radiation source 37R.

Further, as illustrated in FIG. 2A, the radiation emitting unit 37 further comprises a mirror 31 and a filter 33. In a case in which a tube voltage is applied to the radiation source 37R, the radiation source 37R generates the radiation R and emits the generated radiation R to the imaging table 30. The filter 33 is made of a material, such as molybdenum (Mo) or rhodium (Rh), and selectively transmits a desired wavelength component among a plurality of wavelength components included in the radiation R generated by the radiation source 37R.

In a case in which a voltage is applied to the visible light source 37V, the visible light source 37V is turned on to generate visible light V and emits the generated visible light V. For example, in the mammography apparatus 10 according to this embodiment, the visible light source 37V is provided outside an irradiation field 102 (see FIG. 2B) of the radiation R.

The mirror 31 reflects the visible light V emitted from the visible light source 37V to the imaging surface 30A of the imaging table 30 such that the irradiation field 102 which is a region irradiated with the radiation R is indicated by the visible light V. The mirror 31 transmits the radiation R emitted from the radiation source 37R.

The collimator 38 has a function of limiting the irradiation field 102 of the radiation R and the visible light V. As illustrated in FIG. 2A, the collimator 38 is provided between the mirror 31 and the imaging table 30. FIG. 2B is a perspective view illustrating an example of the configuration of the collimator 38 according to this embodiment. As illustrated in FIG. 2B, for example, the collimator 38 according to this embodiment includes four blades 38A, 38B, 38C, and 38D. Each of the blades 38A to 38D is a plate-shaped member which has a rectangular shape in a plan view and is made of a material, such as lead or tungsten, that shields the radiation R. In the collimator 38, one side surface of the blade 38A faces one side surface of the blade 38B, and one side surface of the blade 38C faces one side surface of the blade 38D. Further, in the collimator 38, an opening portion 100 that has a rectangular shape in a plan view is formed by the side surfaces of the blades 38A to 38D which face each other.

In the collimator 38, each of the blades 38A to 38D is moved by a driving unit (not illustrated) including, for example, a motor. The blade 38A and the blade 38B can be moved in the y direction of FIG. 2B, and the blade 38C and the blade 38D can be moved in the x direction of FIG. 2B which intersects the y direction. Further, in the collimator 38 according to this embodiment, the movable range of the blades 38A to 38D is a range from a state in which the leading ends of the blades facing each other come into contact with each other, that is, a state in which the opening portion 100 is fully closed to a state in which the opening portion 100 keeps a rectangular shape in a plan view and has the maximum area. The irradiation field 102 has a shape and size (area) corresponding to the shape and size (area) of the opening portion 100. In this way, the visible light V is projected in the range of the irradiation field 102 to indicate the irradiation field 102. The mirror 31, the visible light source 37V, and the collimator 38 according to this embodiment are an example of an irradiation field projection unit according to the present disclosure.

In addition, as illustrated in FIG. 2A, the mammography apparatus 10 according to this embodiment comprises the arm portion 32, a base 34, and a shaft portion 35. The arm portion 32 is held by the base 34 so as to be movable in an up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and medio-lateral oblique (MLO) imaging in which the imaging direction is a medio-lateral oblique direction for the breast. In the following description, the position of the radiation source 37R in a case in which the radiation R is emitted from the radiation source 37R to the imaging table 30 in the capture of a radiographic image is referred to as an "imaging position".

In a case in which the CC imaging is performed, the imaging surface 30A is adjusted to a state in which the imaging surface 30A faces the upper side of the mammography apparatus 10 (the head of the subject). Further, in this case, the position of the radiation source 37R is adjusted to the imaging position that faces the imaging surface 30A of the imaging table 30. Therefore, the radiation R is emitted from the radiation source 37R to the breast in a direction from the head to the foot of the subject, and the CC imaging is performed.

In contrast, in a case in which the MLO imaging is performed, the position of the imaging table 30 is adjusted to a state in which the imaging surface 30A is rotated up to a predetermined angle in a range of, for example, 45 degrees or more and less than 90 degrees with respect to the case in which the CC imaging is performed. Specifically, in a case in which an image of the left breast is captured, the imaging surface 30A is inclined to the right. In a case in which an image of the right breast is captured, the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 3) that moves a compression plate 40 compressing the breast in the up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit 42 to compress the breast of the subject between the compression plate 40 and the imaging table 30. As illustrated in FIG. 2A, for the movement direction of the compression plate 40, the direction in which the breast is compressed, that is, the direction in which the compression plate 40 approaches the imaging surface 30A, is referred to as a "compression direction", and the direction in which the compression of the breast is released, that is, the direction in which the compression plate 40 approaches the radiation emitting unit 37, is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression plate detection sensor (see a compression plate detection sensor 44 in FIG. 3). The compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2C:
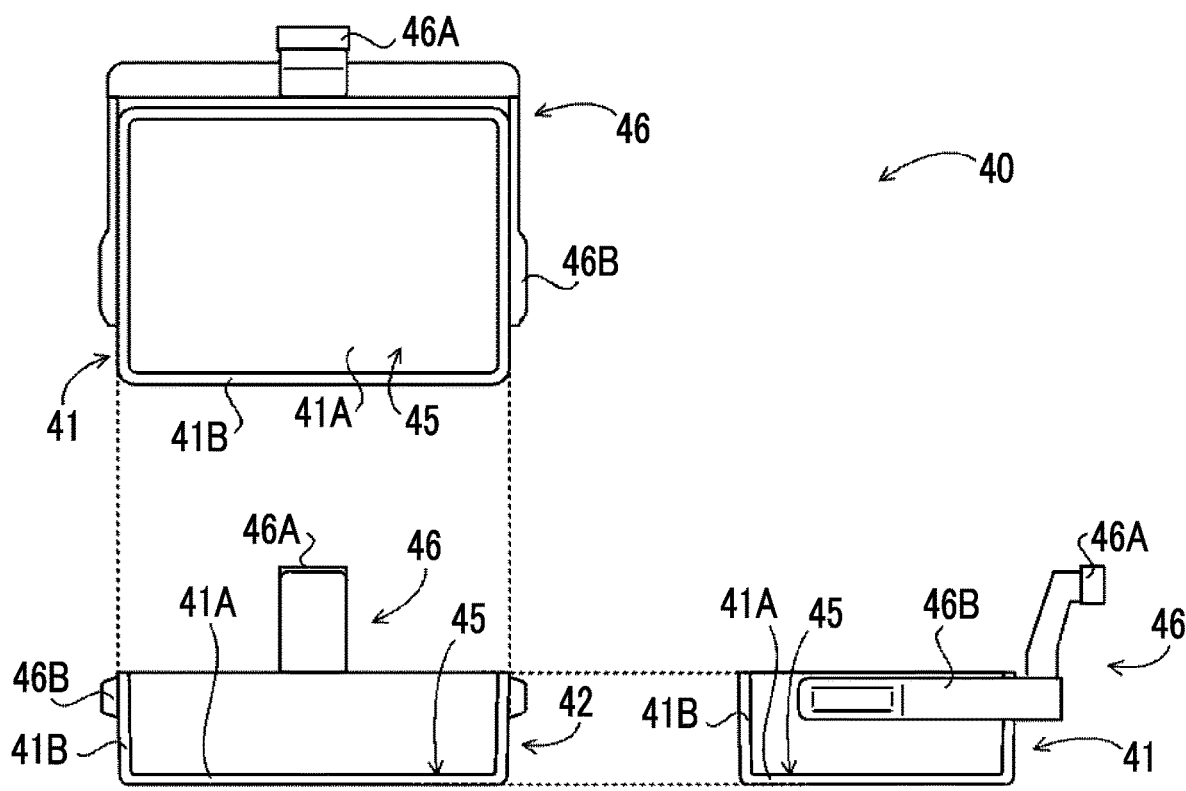
FIG. 2C is a three-view diagram illustrating an example of a compression plate according to the embodiment.

As a specific example, the compression plate 40 that can be attached to the mammography apparatus 10 according to this embodiment will be described with reference to FIG. 2C. FIG. 2C is a three-view diagram illustrating an example of the compression plate 40 according to this embodiment. The three-view diagram illustrated in FIG. 2C includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2C, the compression plate 40 according to this embodiment includes a compression portion 41 and a support portion 46.

The compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height. The compression portion 41 has a projection surface 45 onto which a projection image P is projected by a projector 48 which will be described below. For example, in this embodiment, a surface (upper surface) of the bottom portion 41A of the compression portion 41 which faces the radiation emitting unit 37 is the projection surface 45. In addition, for example, the position of the projection surface 45 of the compression plate 40 is not limited to this embodiment. For example, the projection surface 45 may be a surface of the bottom portion 41A of the compression portion 41 which comes into contact with the breast or a surface of the wall portion 41B.

It is preferable that the compression plate 40 is optically transparent in order to check positioning or a compressed state. In addition, the compression plate 40 is made of a material having high transmittance for the radiation R. Further, in a case in which light is incident on the projection surface 45, most of the light (for example, 90%) is transmitted and a portion (for example, 10%) of the light is specularly reflected from the surface of an object such that an incident angle and a reflection angle are equal to each other, in order to display an image corresponding to the projection image P projected from the projector 48. For example, a surface of the bottom portion 41A of the compression plate 40 which faces the radiation source 37R may be roughened to form the projection surface 45. In addition, for example, a specular reflection sheet may be attached to the surface of the compression plate 40 to form the projection surface 45. Further, in a case in which the projection surface 45 is a smooth surface such as a case in which a specular reflection sheet is attached, a surface of the compression plate 40 that comes into contact with the subject, such as the breast, may be the projection surface 45.

On the other hand, the support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

Further, the projector 48 that projects the projection image P onto the projection surface 45 of the compression plate 40 is provided at a position of the arm portion 32 which is away from the subject below the radiation emitting unit 37. The projector 48 according to this embodiment is an example of an image projection unit according to the present disclosure. Known projectors, such as a liquid crystal projector, a Digital Light Processing (DLP) (registered trademark) projector, and a laser projector, can be used as the projector 48. As illustrated in FIG. 3, the projector 48 according to this embodiment includes a power supply unit 48A and a projection unit 48B. In the projector 48, the turn-on and turn-off of the power supply unit 48A are controlled in response to an instruction from a control unit 20 which will be described below. Further, the projection image P is projected from the projection unit 48B onto the projection surface 45 of the compression plate 40 in response to an instruction from the control unit 20.

Furthermore, the control unit 20, a storage unit 22, an interface (I/F) unit 24, an operation unit 26, and a display unit 27 illustrated in FIG. 3 are provided in the imaging table 30 of the mammography apparatus 10 according to this embodiment. The control unit 20, the storage unit 22, the I/F unit 24, the operation unit 26, the display unit 27, the radiation detector 28, the radiation emitting unit 37, the compression plate driving unit 42, the compression plate detection sensor 44, and the projector 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by the radiation detector 28 and various other kinds of information are stored in the storage unit 22. Examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a projection control program 51 (which will be described below) executed by the CPU 50A are stored in the ROM 50B in advance. The RAM 50C temporarily stores various kinds of data. The CPU 50A according to this embodiment is an example of a processor according to the present disclosure. The projection control program 51 according to this embodiment is an example of a control program according to the present disclosure.

The storage unit 52 stores, for example, projection image data 53A, projection image data 53B, the image data of the radiographic image captured by the mammography apparatus 10, and various other kinds of information. An HDD or an SSD is given as a specific example of the storage unit 52. In addition, hereinafter, in a case in which the projection image data 53A and the projection image data 53B are generically referred to without being distinguished from each other, they are referred to as projection image data 53.

The operation unit 56 is used by the user to input, for example, instructions which are related to the capture of a radiographic image and which include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
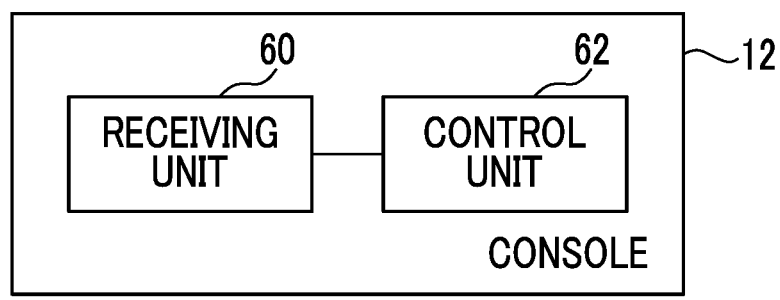
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a receiving unit 60 and a control unit 62. In the console 12 according to this embodiment, the CPU 50A of the control unit 50 executes the projection control program 51 stored in the ROM 50B to function as the receiving unit 60 and the control unit 62.

The receiving unit 60 has a function of receiving an instruction to start the projection of the projection image P for starting the projection of the projection image P onto the projection surface 45. For example, in this embodiment, in a case in which the user wants to start the projection of the projection image P onto the projection surface 45, the user sends instruction to start the projection through the operation unit 26 of the mammography apparatus 10. The mammography apparatus 10 outputs a projection image projection start instruction signal through the I/F unit 24. In a case in which the projection image projection start instruction signal is input to the console 12, the receiving unit 60 receives the instruction to start the projection of the projection image P for starting the projection of the projection image P. The receiving unit 60 outputs projection image projection start information indicating that the instruction to start the projection of the projection image P has been received to the control unit 62.

Further, the receiving unit 60 has a function of receiving an instruction to end the projection of the projection image P for ending the projection of the projection image P onto the projection surface 45. For example, in this embodiment, in a case in which the user wants to end the projection of the projection image P onto the projection surface 45, the user sends instruction to end the projection through the operation unit 26 of the mammography apparatus 10. The mammography apparatus 10 outputs a projection image projection end instruction signal through the I/F unit 24. In a case in which the projection image projection end instruction signal is input to the console 12, the receiving unit 60 receives the instruction to end the projection of the projection image P for ending the projection of the projection image P. The receiving unit 60 outputs projection image projection end information indicating that the instruction to end the projection of the projection image P has been received to the control unit 62.

Further, the receiving unit 60 has a function of receiving an instruction to start the projection of the range of the irradiation field 102 for starting the projection of the range of the irradiation field 102. For example, in this embodiment, in a case in which the user wants to start the projection of the range of the irradiation field 102, the user sends instruction to start the projection through the operation unit 26 of the mammography apparatus 10. The mammography apparatus 10 outputs an irradiation field projection start instruction signal through the I/F unit 24. In a case in which the irradiation field projection start instruction signal is input to the console 12, the receiving unit 60 receives the instruction to start the projection of the range of the irradiation field 102 for starting the projection of the range of the irradiation field 102. The receiving unit 60 outputs irradiation field projection start information indicating that the instruction to start the projection of the range of the irradiation field 102 has been received to the control unit 62.

Further, the receiving unit 60 has a function of receiving an instruction to end the projection of the range of the irradiation field 102 for ending the projection of the range of the irradiation field 102. For example, in this embodiment, in a case in which the user wants to end the projection of the range of the irradiation field 102, the user sends instruction to end the projection through the operation unit 26 of the mammography apparatus 10. The mammography apparatus 10 outputs an irradiation field projection end instruction signal through the I/F unit 24. In a case in which the irradiation field projection end instruction signal is input to the console 12, the receiving unit 60 receives the instruction to end the projection of the range of the irradiation field 102 for ending the projection of the range of the irradiation field 102. The receiving unit 60 outputs irradiation field projection end information indicating that the instruction to end the projection of the range of the irradiation field 102 has been received to the control unit 62. In addition, hereinafter, in some cases, the projection of the range of the irradiation field 102 is simply referred to as "projection of the irradiation field 102".

The control unit 62 has a function of controlling the mammography apparatus 10 such that the projection of the projection image P and the projection of the irradiation field 102 are switched. The projector 48 emits projection light to project the projection image P. Further, the visible light source 37V emits visible light to project the irradiation field 102. In this way, in both the projection of the projection image P by the projector 48 and the projection of the irradiation field 102 by the visible light source 37V, light is emitted to the compression plate 40 (imaging table 30). Therefore, in a case in which the projection image P and the irradiation field 102 are projected at the same time, for example, the projection image P may not be displayed due to the visible light V for projecting the irradiation field 102. For this reason, the control unit 62 according to this embodiment switches the projection of the projection image P and the projection of the irradiation field 102 such that the projection light for the projection image P and the visible light for the irradiation field 102 are not emitted at the same time.

Further, the control unit 62 according to this embodiment has a function of displaying the range of the irradiation field 102 using the projection image P in a case in which instruction to project the projection image P is sent while the irradiation field 102 is being projected. As described above, in a case in which the projector 48 emits the projection light to project the projection image P while the irradiation field 102 is being projected, the projection image P may not be displayed due to the visible light V for projecting the irradiation field 102. Therefore, even in a case in which the user wants to further display the projection image P while the irradiation field 102 is being displayed, it may be difficult to display both the irradiation field 102 and the projection image P. For this reason, in a case in which instruction to project the projection image P is sent while the irradiation field 102 is being projected, the control unit 62 according to this embodiment displays the range of the irradiation field 102 using the projection image P, which makes it to possible to display the range of the irradiation field 102 without emitting the visible light V from the visible light source 37V.

Specifically, the control unit 62 according to this embodiment acquires the compression plate identifier read by the compression plate detection sensor 44 from the mammography apparatus 10 in a case in which the projection image P is projected. The control unit 62 acquires any one of the projection image data 53A or the projection image data 53B indicating the projection image P corresponding to the acquired compression plate identifier from the storage unit 52. A projection image for guiding the positioning of the breast is applied as the projection image P according to this embodiment. Specifically, a projection image projected from the projector 48 in order to display an image for guiding at least one of the shape or position of the breast compressed by the compression plate 40 on the projection surface 45 of the compression plate 40 is applied as the projection image P. For example, in this embodiment, an image indicating the skin line of the breast and the position of the nipple in a case in which a standard breast corresponding to the type of the compression plate 40 or the like is compressed to an ideal state is applied as the image for guiding at least one of the shape or position of the breast.

In some cases, the size of the compression portion 41 and the size of the projection surface 45 vary depending on the type of the compression plate 40. Therefore, in this embodiment, the projection image P corresponding to the type of the compression plate 40 is projected from the projector 48. For example, in this embodiment, a plurality of projection image data items corresponding to the projection images P corresponding to the types of the compression plate 40 are stored as the projection image data 53A in the storage unit 52 so as to be associated with the compression plate identifiers. In addition, a plurality of projection image data items that indicate the projection images P corresponding to the types of the compression plate 40 and that include images for displaying the irradiation field 102 are stored as the projection image data 53B in the storage unit 52 so as to be associated with the compression plate identifiers. The control unit 62 acquires the projection image data 53A or the projection image data 53B corresponding to the acquired compression plate identifier from the storage unit 52 and outputs the projection image data to the mammography apparatus 10 through the I/F unit 54.

Figure 5A:
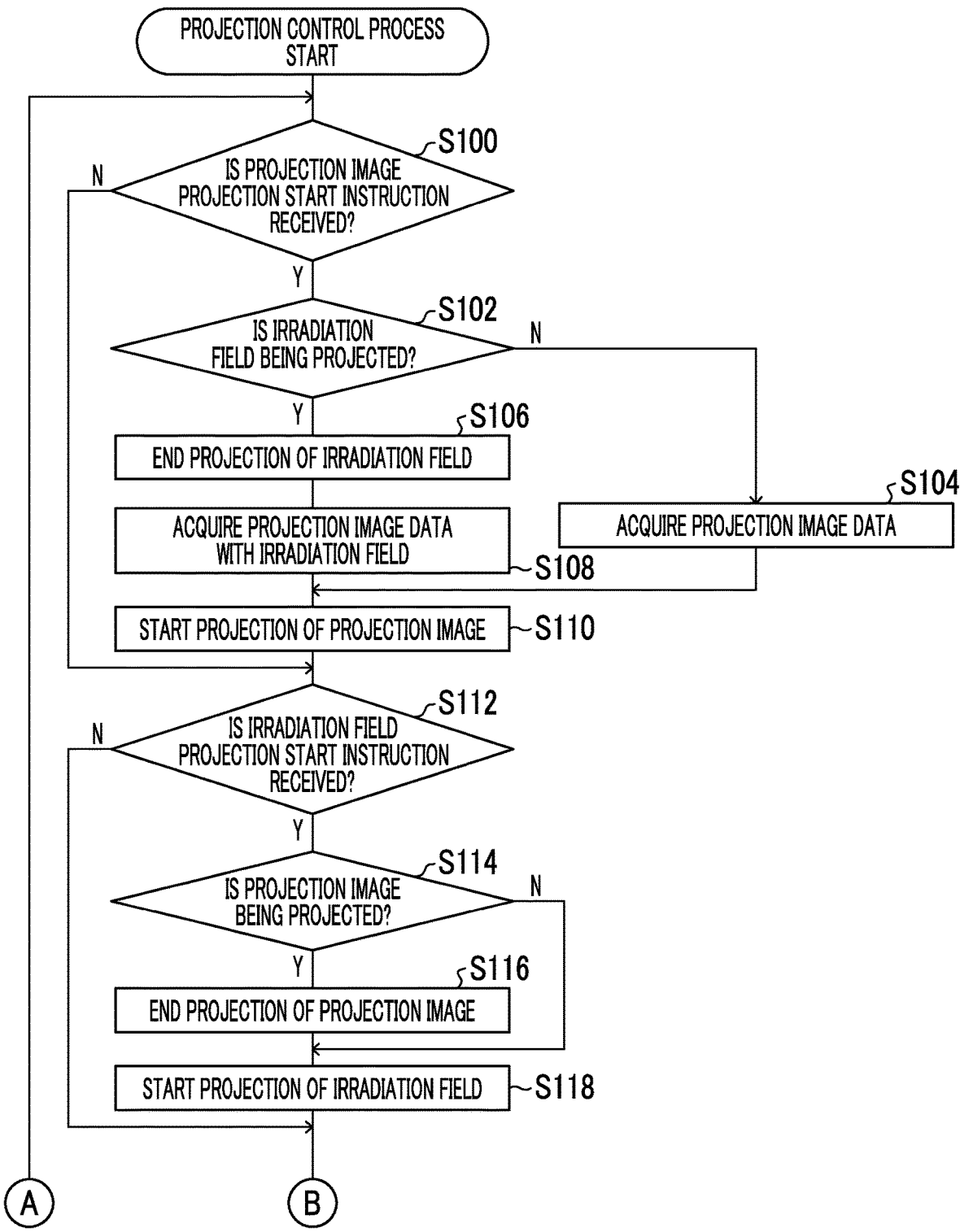
FIGS. 5A and 5B are flowcharts illustrating an example of the flow of a projection control process according to a first embodiment.
Figure 5B:
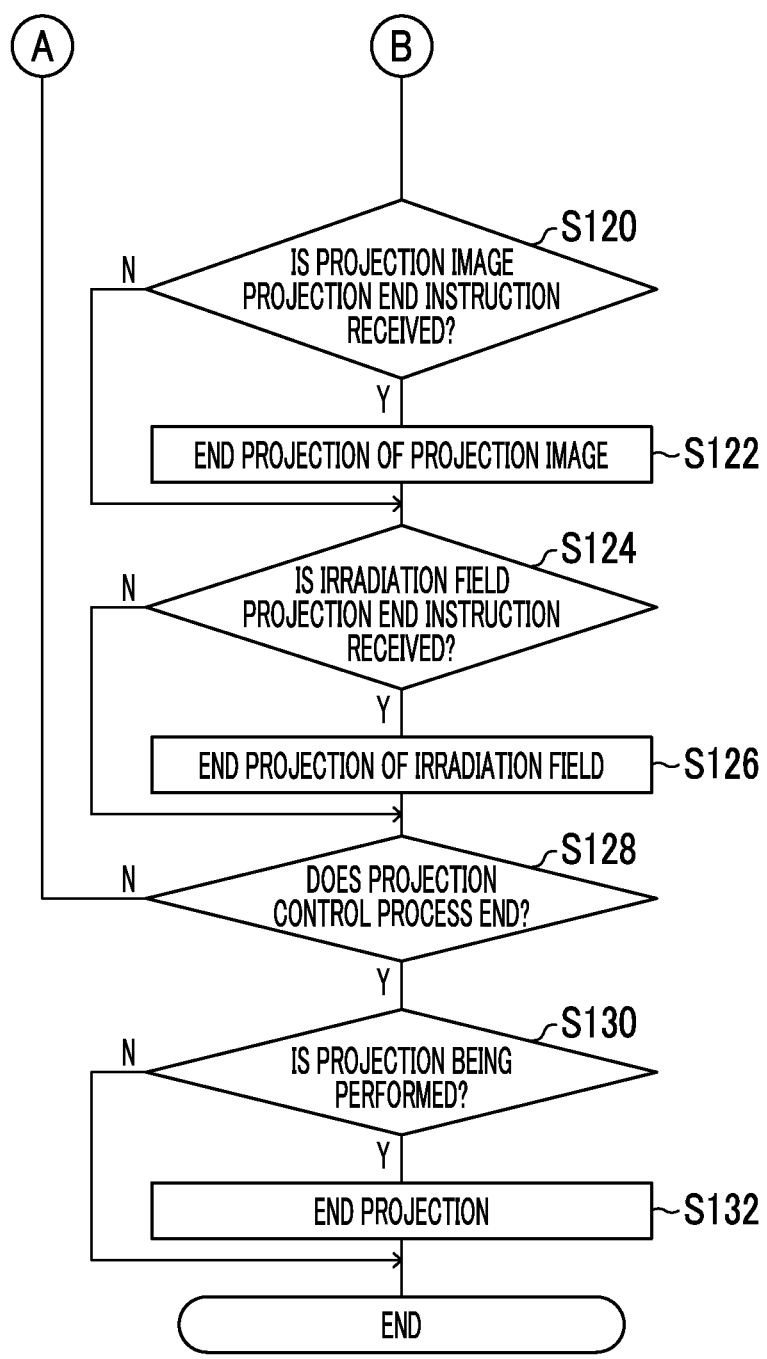

Next, the operation of the console 12 in the projection of the projection image P by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selected imaging menu, a projection control process illustrated in FIGS. 5A and 5B is performed. In the console 12 according to this embodiment, for example, the CPU 50A of the control unit 50 executes the projection control program 51 stored in the ROM 50B to perform the projection control process whose example is illustrated in FIGS. 5A and 5B. FIGS. 5A and 5B are flowcharts illustrating an example of the flow of the projection control process performed in the console 12 according to this embodiment.

In Step S100 of FIGS. 5A and 5B, the control unit 62 determines whether or not the receiving unit 60 has received the instruction to start the projection of the projection image P. As described above, in a case in which the user wants to start the projection of the projection image P onto the projection surface 45, the receiving unit 60 receives the instruction to start the projection of the projection image P. Therefore, in this step, it is determined whether or not the user has sent the instruction to start the projection of the projection image P. In a case in which the receiving unit 60 has not received the instruction to start the projection of the projection image P, the determination result in Step S100 is "No", and the process proceeds to Step S112. On the other hand, in a case in which the receiving unit 60 has received the instruction to start the projection of the projection image P, the determination result in Step S100 is "Yes", and the process proceeds to Step S102.

In Step S102, the control unit 62 determines whether or not the irradiation field 102 is being projected. In a case in which the irradiation field 102 is not being projected, the determination result in Step S102 is "No", and the process proceeds to Step S104. In Step S104, the control unit 62 acquires projection image data for projecting the projection image P and then proceeds to Step S110. Specifically, as described above, the control unit 62 acquires the compression plate identifier from the mammography apparatus 10 and acquires the projection image data 53 corresponding to the acquired compression plate identifier from the storage unit 52.

On the other hand, in a case in which the irradiation field 102 is being projected, the determination result in Step S102 is "Yes", and the process proceeds to Step S106. In Step S106, the control unit 62 ends the projection of the irradiation field 102. Specifically, the control unit 62 outputs an irradiation field projection end signal for ending the projection of the irradiation field 102 to the mammography apparatus 10 through the I/F unit 54. In the mammography apparatus 10, in a case in which the irradiation field projection end signal is input, the control unit 20 turns off the visible light source 37V to stop the emission of the visible light V, thereby ending the projection of the irradiation field 102.

Then, in Step S108, the control unit 62 acquires the projection image data 53B for projecting the projection image P capable of displaying the range of the irradiation field 102 from the storage unit 52. In addition, in some cases, the range of the irradiation field 102 varies depending on, for example, the size of the breast or the size of the compression plate 40. For example, in this embodiment, the range of the irradiation field 102 is determined on the basis of the imaging menu. Therefore, the control unit 62 specifies the range of the irradiation field 102 with reference to the imaging menu and acquires the projection image data 53B, which can display the specified range of the irradiation field 102 and corresponds to the acquired compression plate identifier, from the storage unit 52.

Then, in Step S110, the control unit 62 starts the projection of the projection image P. Specifically, the control unit 62 outputs the projection image data 53A acquired in Step S104 or the projection image data 53B acquired in Step S108 to the mammography apparatus 10 through the I/F unit 54. In the mammography apparatus 10, in a case in which the projection image data 53 is input, the control unit 20 performs control to direct the projection unit 48B of the projector 48 to project the projection image P corresponding to the projection image data 53. A display image corresponding to the projection image P is displayed on the projection surface 45 of the compression plate 40 attached to the compression unit 36 of the mammography apparatus 10 by this control. In this embodiment, as described above, an image indicating the skin line of the breast and the position of the nipple is displayed on the projection surface 45 of the compression plate 40.

Figure 6A:
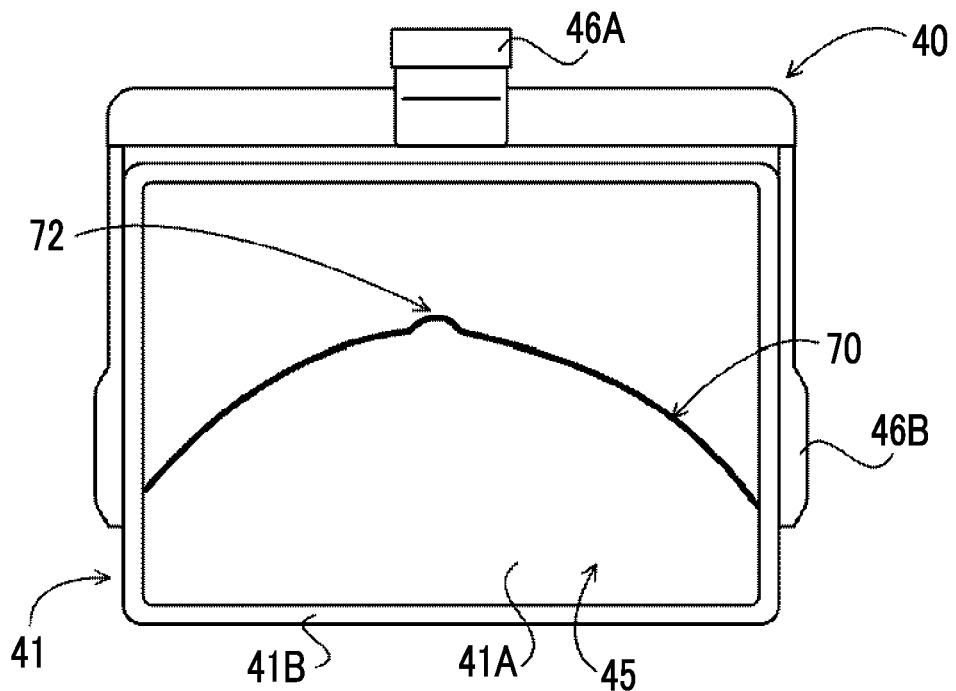
FIG. 6A is a diagram illustrating an example of a skin line and the position of a nipple displayed on a projection surface of the compression plate according to a projection image.

FIG. 6A illustrates an example of a skin line 70 and a position 72 of the nipple which are displayed on the projection surface 45 of the compression plate 40 according to the projection image P projected by the projection image data 53A. The user compresses the breast of the subject positioned with reference to the displayed skin line 70 and the displayed position 72 of the nipple with the compression plate 40.

Figure 6B:
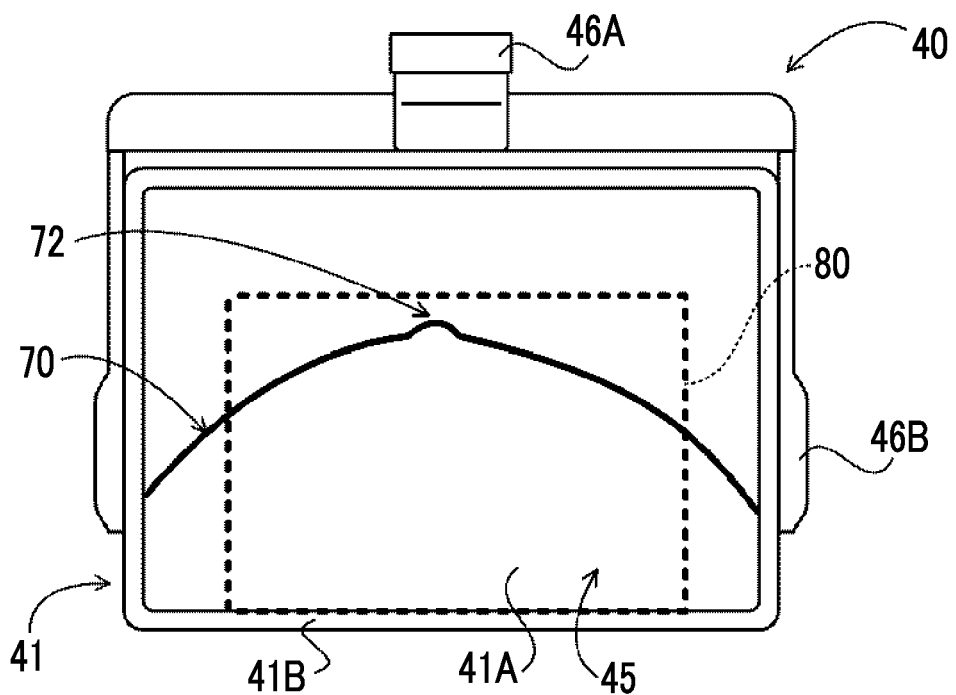
FIG. 6B is a diagram illustrating an example of the skin line, the position of the nipple, and an irradiation field boundary line displayed on the projection surface of the compression plate according to the projection image.

Further, FIG. 6B illustrates an example of the skin line 70, the position 72 of the nipple, and an irradiation field boundary line 80 displayed on the projection surface 45 of the compression plate 40 according to the projection image P projected by the projection image data 53B. The irradiation field boundary line 80 is a line (dotted line) indicating the boundary between the inside and outside of the irradiation field 102. In the example illustrated in FIG. 6B, the inside surrounded by the irradiation field boundary line 80 is the range of the irradiation field 102. The user compresses the breast of the subject positioned with reference to the displayed skin line 70, the displayed position 72 of the nipple, and the displayed irradiation field boundary line 80 with the compression plate 40.

Then, in Step S112, the control unit 62 determines whether or not the receiving unit 60 has received the instruction to start the projection of the irradiation field 102. As described above, in a case in which the user wants to start the projection of the range of the irradiation field 102, the receiving unit 60 receives the instruction to start the projection of the irradiation field 102. Therefore, in this step, it is determined whether or not the user has sent instruction to start the projection of the irradiation field 102. In a case in which the receiving unit 60 has not received the instruction to start the projection of the irradiation field 102, the determination result in Step S112 is "No", and the process proceeds to Step S120. On the other hand, in a case in which the receiving unit 60 has received the instruction to start the projection of the irradiation field 102, the determination result in Step S112 is "Yes", and the process proceeds to Step S114.

In Step S114, the control unit 62 determines whether or not the projection image P is being projected. In a case in which the projection image P is not being projected, the determination result in Step S114 is "No", and the process proceeds to Step S118. On the other hand, in a case in which the projection image P is being projected, the determination result in Step S114 is "Yes", and the process proceeds to Step S116.

In Step S116, the control unit 62 ends the projection of the projection image P. Specifically, the control unit 62 outputs a projection image projection end signal for ending the projection of the projection image P to the mammography apparatus 10 through the I/F unit 54. In the mammography apparatus 10, in a case in which the projection image projection end signal is input, the control unit 20 ends the projection of the projection image P by the projection unit 48B of the projector 48. Specifically, the emission of the projection light for projecting the projection image P is stopped. In a case in which the projection of the projection image P is ended, the supply of power to the power supply unit 48A is cut off to turn off the power supply unit 48A.

Then, in Step S118, the control unit 62 starts the projection of the irradiation field 102. Specifically, the control unit 62 outputs a projection start signal for projecting the irradiation field 102 to the mammography apparatus 10 through the I/F unit 54. In the mammography apparatus 10, in a case in which the projection start signal is input, the control unit 20 performs control that turns on the visible light source 37V to irradiate the range of the irradiation field 102 with the visible light V, thereby projecting the range of the irradiation field 102. The range of the irradiation field 102 is displayed on the compression plate 40 attached to the compression unit 36 of the mammography apparatus 10 by this control.

Figure 6C:
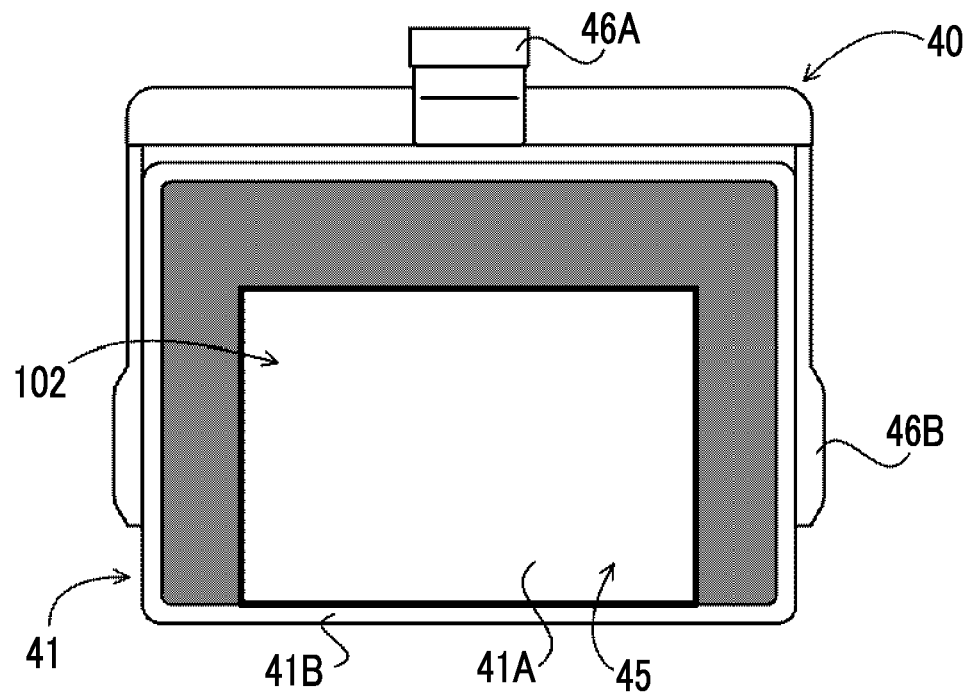
FIG. 6C is a diagram illustrating an example of an irradiation field displayed on the compression plate.

FIG. 6C illustrates an example of the irradiation field 102 displayed on the compression plate 40. The user determines, for example, whether or not the positioning of the breast of the subject is appropriate with reference to the displayed irradiation field 102.

Then, in Step S120, the control unit 62 determines whether or not the receiving unit 60 has received the instruction to end the projection of the projection image P. As described above, in a case in which the user wants to end the projection of the projection image P onto the projection surface 45, the receiving unit 60 receives the instruction to end the projection of the projection image P. Therefore, in this step, it is determined whether or not the user has sent instruction to end the projection of the projection image P. In a case in which the receiving unit 60 has not received the instruction to end the projection of the projection image P, the determination result in Step S120 is "No", and the process proceeds to Step S124. On the other hand, in a case in which the receiving unit 60 has received the instruction to end the projection of the projection image P, the determination result in Step S120 is "Yes", and the process proceeds to Step S122. In Step S122, the control unit 62 ends the projection of the projection image P as in Step S116.

Then, in Step S124, the control unit 62 determines whether or not the receiving unit 60 has received the instruction to end the projection of the irradiation field 102. As described above, in a case in which the user wants to end the projection of the irradiation field 102, the receiving unit 60 receives the instruction to end the projection of the irradiation field 102. Therefore, in this step, it is determined whether or not the user has sent instruction to end the projection of the irradiation field 102. In a case in which the receiving unit 60 has not received the instruction to end the projection of the irradiation field 102, the determination result in Step S124 is "No", and the process proceeds to Step S128. On the other hand, in a case in which the receiving unit 60 has received the instruction to end the projection of the irradiation field 102, the determination result in Step S124 is "Yes", and the process proceeds to Step S126. In Step S126, the control unit 62 ends the projection of the irradiation field 102 as in Step S106.

Then, in Step S128, the control unit 62 determines whether or not to end the projection control process. In this embodiment, the projection control process is ended in a case in which end conditions are satisfied. In a case in which the compression of the breast is completed, the user sends instruction to emit the radiation R. In a case in which the mammography apparatus 10 receives an instruction to emit the radiation R, the radiation R is emitted from the radiation source 37R of the radiation emitting unit 37, and the radiation detector 28 captures a radiographic image of the breast. Therefore, for example, in this embodiment, a case in which the user has sent instruction to emit the radiation R is applied as the end condition. In a case in which the user has not sent instruction to emit the radiation R, the determination result in Step S128 is "No", and the process returns to Step S100. Then, the processes in Steps S100 to S126 are repeated. On the other hand, in a case in which the user has sent instruction to emit the radiation R, the determination result in Step S128 is "Yes", and the process proceeds to Step S130.

In Step S130, the control unit 62 determines whether or not the projection image P or the irradiation field 102 is being projected. In a case in which neither the projection image P nor the irradiation field 102 is being projected, the determination result in Step S130 is "No", and the projection control process illustrated in FIGS. 5A and 5B ends.

On the other hand, in a case in which the projection image P or the irradiation field 102 is being projected, the determination result in Step S130 is "Yes", and the process proceeds to Step S132. In Step S132, the control unit 62 ends the projection of the projection image P or the irradiation field 102 that is being projected. Specifically, in a case in which the projection image P is being projected, the control unit 62 ends the projection of the projection image P as in Step S116. In a case in which the irradiation field 102 is being projected, the control unit 62 ends the projection of the irradiation field 102 as in Step S106. In a case in which the process in Step S132 ends, the projection control process illustrated in FIGS. 5A and 5B ends.

As described above, the console 12 according to this embodiment controls the mammography apparatus 10 such that the projection of the projection image P and the projection of the irradiation field 102 are switched. Therefore, in the console 12 according to this embodiment, the projection light for projecting the projection image P and the visible light V for projecting the irradiation field 102 are not emitted at the same time. As a result, according to the console 12 of this embodiment, it is possible to prevent the projection image P and the range of the irradiation field 102 from being unrecognizable.

Figure 7A:
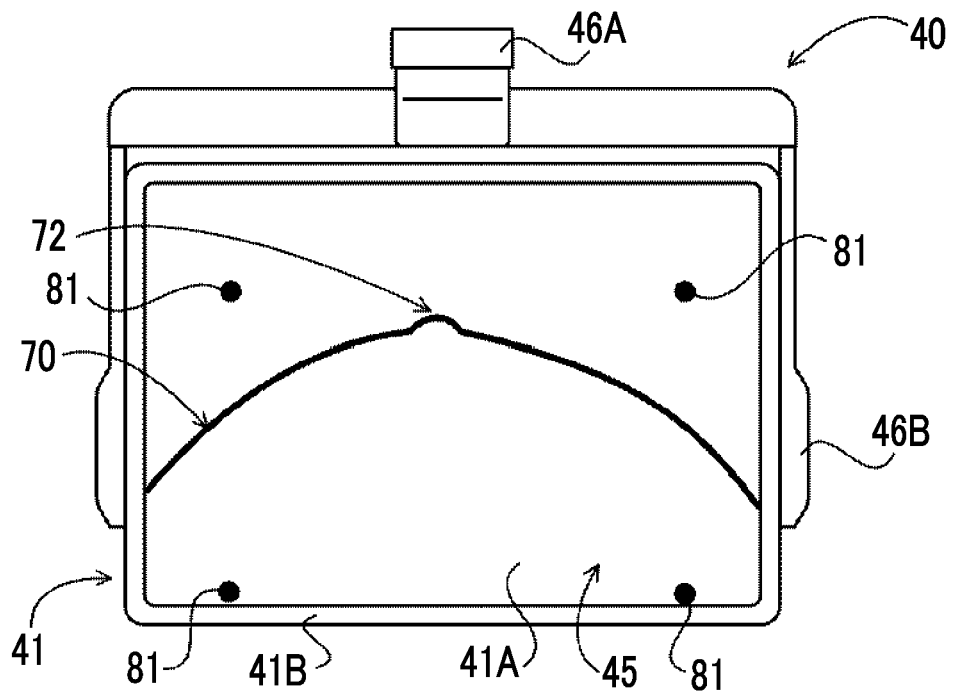
FIG. 7A is another example of an image for displaying the irradiation field using the projection of the projection image.
Figure 7B:
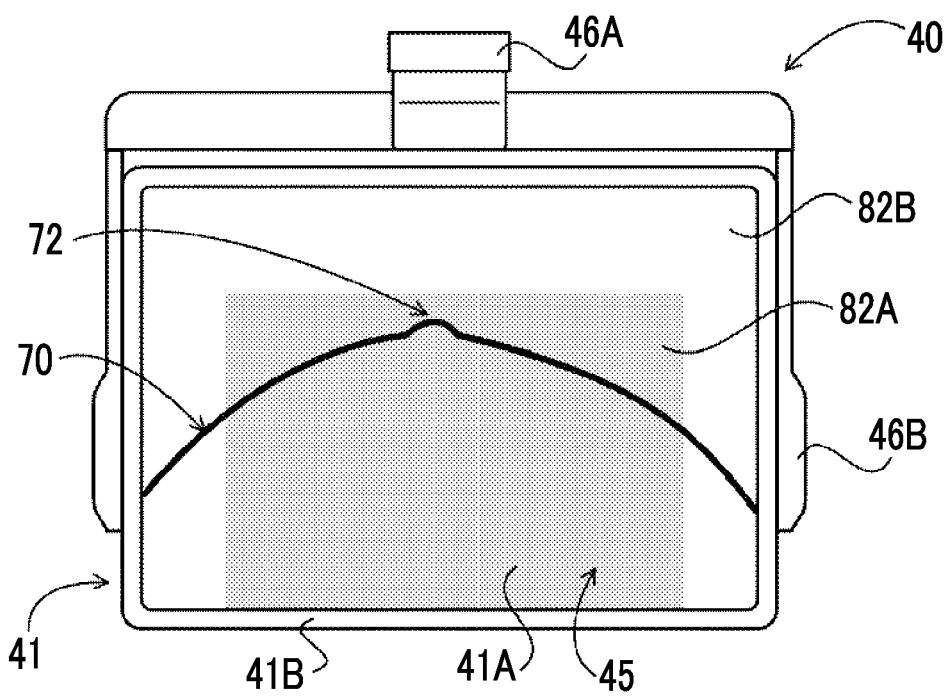
FIG. 7B is still another example of the image for displaying the irradiation field using the projection of the projection image.

In addition, the irradiation field boundary line 80 (see FIG. 6B) has been described as the image for displaying the irradiation field 102. However, the image for displaying the irradiation field 102 is not limited to this aspect. For example, in the irradiation field boundary line 80 illustrated in FIG. 6B, the entire boundary line of the irradiation field 102 is represented by a line. However, a portion of the boundary line may be represented by a line. Further, for example, as illustrated in FIG. 7A, a mark 81 indicating the boundary between the inside and outside of the irradiation field 102 may be applied as the image for displaying the irradiation field 102. FIG. 7A illustrates an example of the aspect in which the mark 81 is displayed at each of four corners of the rectangular irradiation field 102 to display the irradiation field 102. Further, for example, as illustrated in FIG. 7B, an image in which at least one of brightness or saturation is different between a region within the range of the irradiation field 102 and a region outside the range of the irradiation field 102 may be applied. In the example illustrated in FIG. 7B, an aspect in which the brightness and saturation of a region 82A within the range of the irradiation field 102 are lower than the brightness and saturation of a region 82B outside the range of the irradiation field 102 is illustrated. In addition, in a case in which brightness and saturation are different in this way, for example, the brightness and saturation may be decreased or increased for each pixel within the range of the irradiation field 102 in the projection image P represented by the projection image data 53A without using the projection image data 53B.

Further, in this embodiment, both the brightness and the saturation are controlled. However, only one of the brightness and the saturation may be controlled. Further, luminance may be controlled similarly to brightness and saturation.

Second Embodiment

In this embodiment, a difference in the control of each of the projection of the projection image P and the projection of the irradiation field 102 from the first embodiment will be described.

In addition, the configuration of the console 12 according to this embodiment differs from that of the console 12 according to the first embodiment (see FIG. 3) in that the projection image data 53B is not stored in the storage unit 52 of the console 12. Further, since the functions of the control unit 62 included in the console 12 according to this embodiment are different from those of the control unit 62 (see FIG. 4) according to the first embodiment, the functions of the control unit 62 according to this embodiment will be described, and the description of the same configuration will not be repeated.

In a case in which the receiving unit 60 receives both a projection start instruction for projecting the projection image P and a projection start instruction for projecting the irradiation field 102, the control unit 62 according to this embodiment has a function of performing control to highlight display by the projection start instruction received later more than display by the projection start instruction received first. Specifically, in a case in which the receiving unit 60 receives the projection start instruction for projecting the irradiation field 102 while the projection image P is being projected, the control unit 62 performs control to make a display image displayed by the projection image P less noticeable than a display image displayed by the projection image P in a case in which the projection start instruction for projecting the irradiation field 102 is not received. Further, in a case in which the receiving unit 60 receives the projection start instruction for projecting the projection image P while the irradiation field 102 is being projected, the control unit 62 performs control to make the display of the irradiation field 102 less noticeable than the irradiation field 102 displayed in a case in which the projection start instruction for projecting the projection image P is not received.

Figure 8A:
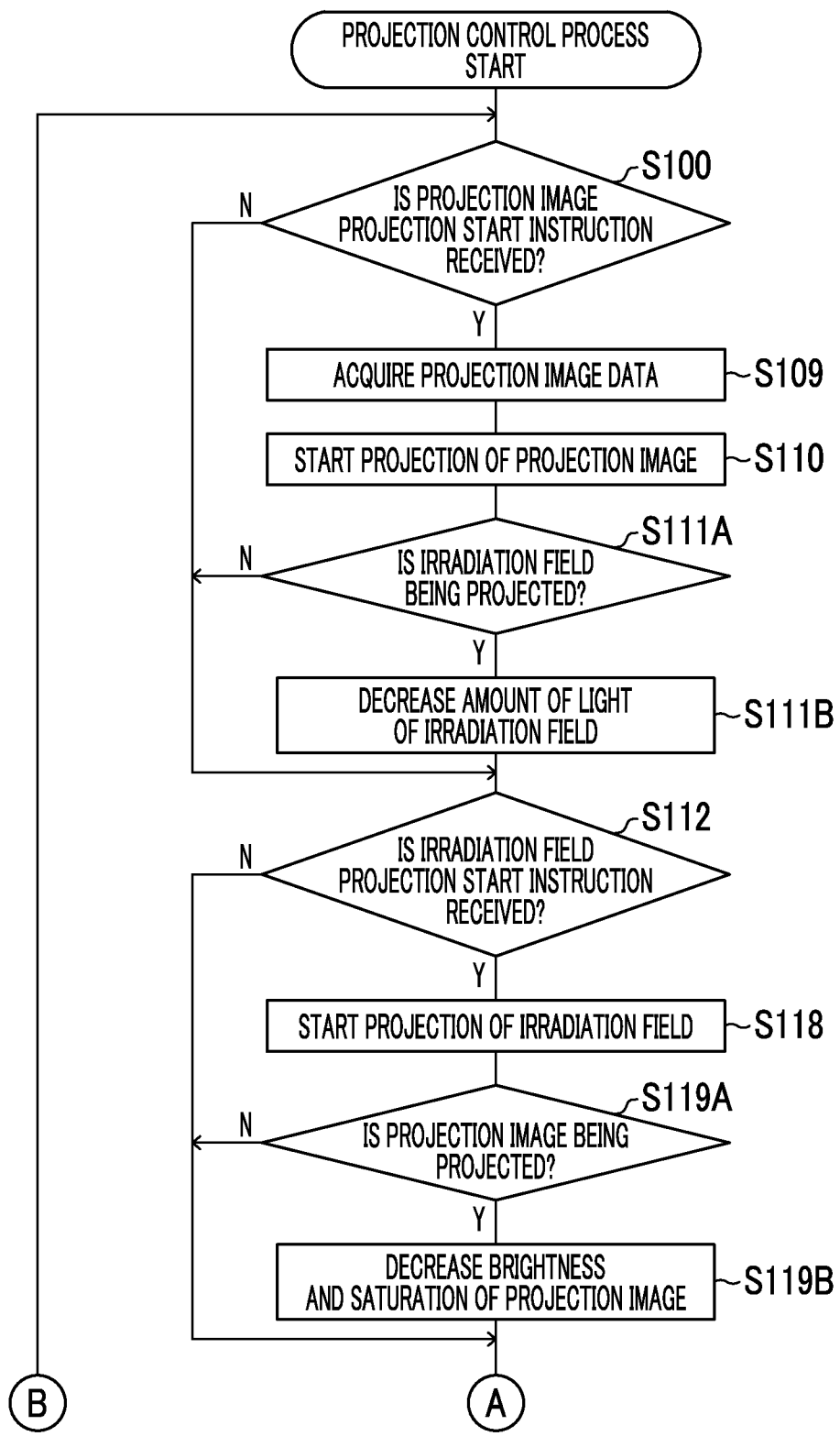
FIGS. 8A and 8B are flowcharts illustrating an example of the flow of a projection control process according to a second embodiment.
Figure 8B:
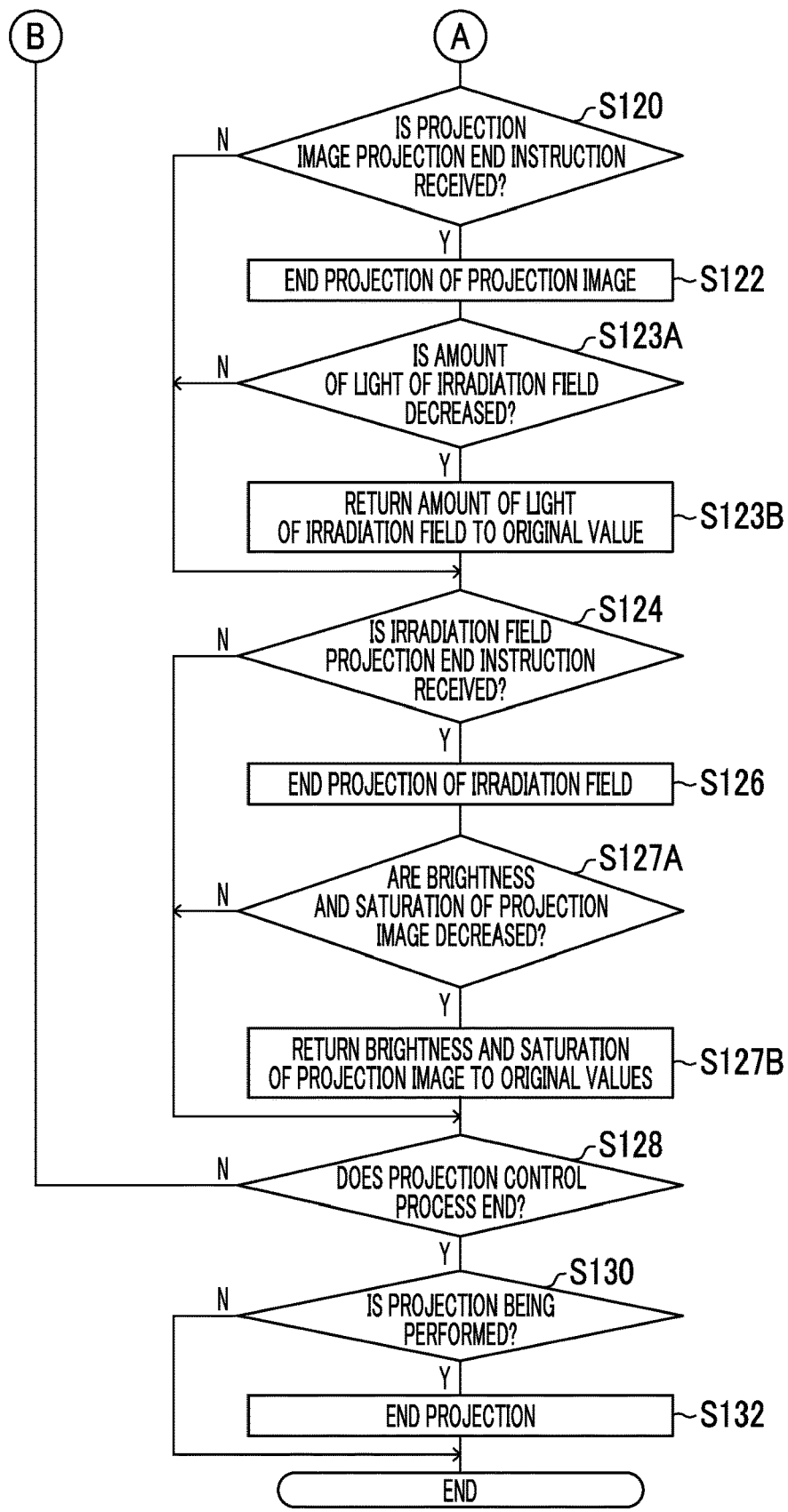

Further, since a projection control process performed in the console 12 in this embodiment differs from that in the first embodiment, the projection control process according to this embodiment will be described. FIGS. 8A and 8B are flowcharts illustrating an example of the flow of the projection control process performed in the console 12 according to this embodiment.

As illustrated in FIGS. 8A and 8B, the projection control process according to this embodiment differs from the projection control process (see FIGS. 5A and 5B) according to the first embodiment in that it comprises a process in Step S109 instead of the processes in Steps S102 to S108 and comprises processes in Steps S111A and S111B between Step S110 and Step S112.

In this embodiment, in a case in which the receiving unit 60 receives an instruction to start the projection of the projection image P (the determination result in Step S100 is "Yes"), in the next Step S109, the control unit 62 acquires the projection image data 53 corresponding to the compression plate identifier acquired from the mammography apparatus 10 from the storage unit 52 as in Step S104 of the projection control process according to the first embodiment.

Further, as illustrated in FIGS. 8A and 8B, in Step S111A, the control unit 62 determines whether or not the irradiation field 102 is being projected. In a case in which the irradiation field 102 is not being projected, the determination result in Step S111A is "No", and the process proceeds to Step S112. On the other hand, in a case in which the irradiation field 102 is being projected, the determination result in Step S111A is "Yes", and the process proceeds to Step S111B.

In Step S111B, the control unit 62 decreases the amount of light of the irradiation field 102 that is being projected. Specifically, the control unit 62 outputs a light amount decrease instruction for decreasing the amount of light of the irradiation field 102 to the mammography apparatus 10 through the I/F unit 54. In the mammography apparatus 10, in a case in which the light amount decrease instruction is input, the control unit 20 decreases the amount of light emitted from the visible light source 37V to dim the visible light V emitted from the visible light source 37V. Here, how much the amount of visible light V is decreased is not particularly limited. However, the amount of light is set such that a display image displayed according to the projection image P is more highlighted (noticeable) than the displayed irradiation field 102.

Further, as illustrated in FIGS. 8A and 8B, the projection control process according to this embodiment differs from the projection control process (see FIGS. 5A and 5B) according to the first embodiment in that it does not comprise the processes in Steps S114 and S116 and comprises processes in Steps S119A and S119B between Steps S118 and S120.

In this embodiment, in a case in which the receiving unit 60 receives the instruction to start the projection of the irradiation field 102, the determination result in Step S112 is "Yes", and the process proceeds to Step S118.

Further, as illustrated in FIGS. 8A and 8B, in Step S119A, the control unit 62 determines whether or not the projection image P is being projected. In a case in which the projection image P is not being projected, the determination result in Step S119A is "No", and the process proceeds to Step S120. On the other hand, in a case in which the projection image P is being projected, the determination result in Step S119A is "Yes", and the process proceeds to Step S119B.

In Step S119B, the control unit 62 decreases the brightness and saturation of the projection image P that is being projected. Specifically, the control unit 62 outputs a brightness and saturation decrease instruction for reducing the brightness and saturation of the display image displayed according to the projection image P to the mammography apparatus 10 through the I/F unit 54. In the mammography apparatus 10, in a case in which the brightness and saturation decrease instruction is input, the control unit 20 decreases the brightness and saturation of the pixels of the projection unit 48B of the projector 48. Here, how much the brightness and saturation of the projection image P are decreased is not particularly limited. However, the brightness and saturation are set such that the displayed irradiation field 102 is more highlighted (noticeable) than the display image displayed according to the projection image P.

Further, as illustrated in FIGS. 8A and 8B, the projection control process according to this embodiment differs from the projection control process (see FIGS. 5A and 5B) according to the first embodiment in that it comprises processes in Steps S123A and S123B between Steps S122 and S124.

In this embodiment, after the control unit 62 ends the projection of the projection image P (S122), it determines whether or not the amount of light of the irradiation field 102 is being decreased in Step S123A. Specifically, the control unit 62 determines whether or not the irradiation field 102 is projected in a state in which the amount of visible light V is decreased by the process in Step S111B. In a case in which the amount of light of the irradiation field 102 is not being decreased, the determination result in Step S123A is "No", and the process proceeds to Step S124. On the other hand, in a case in which the amount of light of the irradiation field 102 is being decreased, the determination result in Step S123A is "Yes", and the process proceeds to Step S123B.

In Step S123B, the control unit 62 returns the amount of light of the irradiation field 102 which is being decreased to the original value. Specifically, the control unit 62 outputs a light amount increase instruction for returning the amount of light of the irradiation field 102 to the original value to the mammography apparatus 10 through the I/F unit 54. In the mammography apparatus 10, in a case in which the light amount increase instruction is input, the control unit 20 increases the amount of light of the visible light source 37V to return the amount of visible light V decreased by the process in Step S111B to the original value. In other words, the amount of visible light V emitted to project the irradiation field 102 is returned to the amount of light before the projection of the projection image P is started.

In addition, as illustrated in FIGS. 8A and 8B, the projection control process according to this embodiment differs from the projection control process (see FIGS. 5A and 5B) according to the first embodiment in that it comprises processes in Steps S127A and S127B between Steps S126 and S128.

In this embodiment, after the control unit 62 ends the projection of the irradiation field 102 (S126), it determines whether or not the brightness and saturation of the projection image P are being decreased in Step S127A. Specifically, the control unit 62 determines whether or not the projection image P is projected in a state in which the brightness and saturation are decreased by the process in Step S119B. In a case in which the brightness and saturation of the projection image P are not being decreased, the determination result in Step S127A is "No", and the process proceeds to Step S128. On the other hand, in a case in which the brightness and saturation of the projection image P are being decreased, the determination result in Step S127A is "Yes", and the process proceeds to Step S127B.

In Step S127B, the control unit 62 returns the brightness and saturation of the projection image P which are being decreased to the original values. Specifically, the control unit 62 outputs a brightness and saturation increase instruction for returning the brightness and saturation of the projection image P to the original values to the mammography apparatus 10 through the I/F unit 54. In the mammography apparatus 10, in a case in which the brightness and saturation increase instruction is input, the control unit 20 returns the brightness and saturation of the pixels of the projection unit 48B of the projector 48 to the brightness and saturation before the projection of the irradiation field 102 is started.

It can be considered that the user currently wants to display one of the projection image P and the irradiation field 102 according to the instruction received later. Therefore, in the console 12 according to this embodiment, in a case in which both the instruction to start the projection of the projection image P and the instruction to start the projection of the irradiation field 102 are received, projection corresponding to the instruction received later is highlighted. Therefore, in this embodiment, in a state in which the projection of the projection image P and the projection of the irradiation field 102 are performed at the same time, it is possible to highlight one of the display image corresponding to the projection image P and the irradiation field 102 that the user wants to display. Therefore, according to the console 12 of this embodiment, it is possible to prevent the projection image P and the range of the irradiation field 102 desired by the user from being unrecognizable.

In addition, in the above-described embodiment, the aspect has been described in which, in a case in which both the instruction to start the projection of the projection image P and the instruction to start the projection of the irradiation field 102 are received, projection corresponding to the instruction received first is unnoticeable as the process for highlighting projection corresponding to the instruction received later. In other words, in the above-described embodiment, the aspect has been described in which the projection corresponding to the instruction received first is less noticeable than a usual projection state such that the projection corresponding to the instruction received later is noticeable even in a case in which the projection corresponding to the instruction received later is performed in the same manner as usual. However, the process for highlighting the projection corresponding to the instruction received later is not limited to this aspect. For example, at least one of the brightness or saturation of the projection image P and the amount of light of the irradiation field 102 may be controlled such that the projection corresponding to the instruction received later is relatively highlighted. For example, the following Modification Example 1 or Modification Example 2 may be used, or any one of the above-mentioned aspects (see FIGS. 8A and 8B), the following Modification Example 1, or the following Modification Example 2 may be combined.

Modification Example 1

Figure 8C:
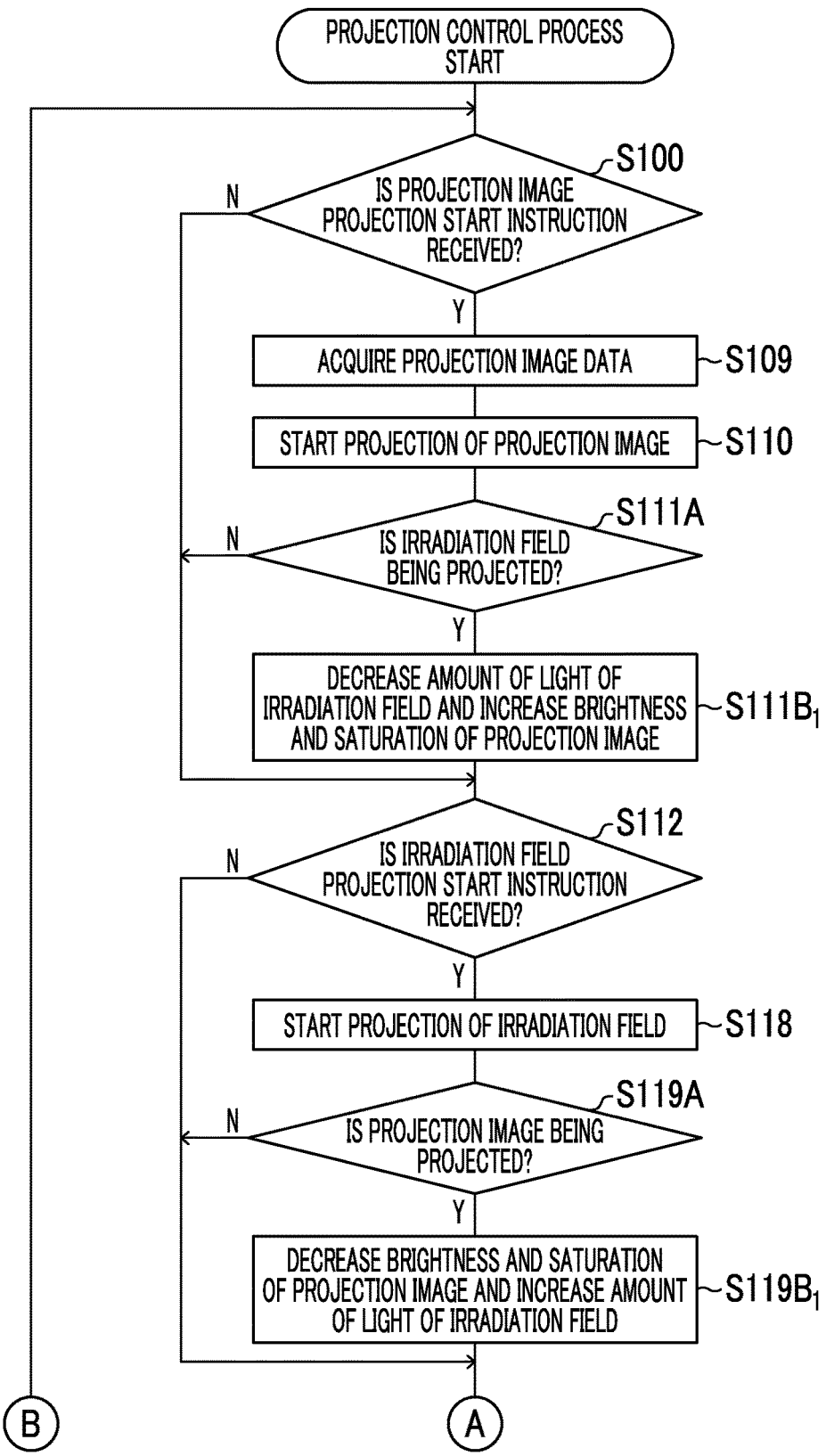
FIGS. 8C and 8D are flowcharts illustrating an example of the flow of a projection control process according to Modification Example 1 of the second embodiment.
Figure 8D:
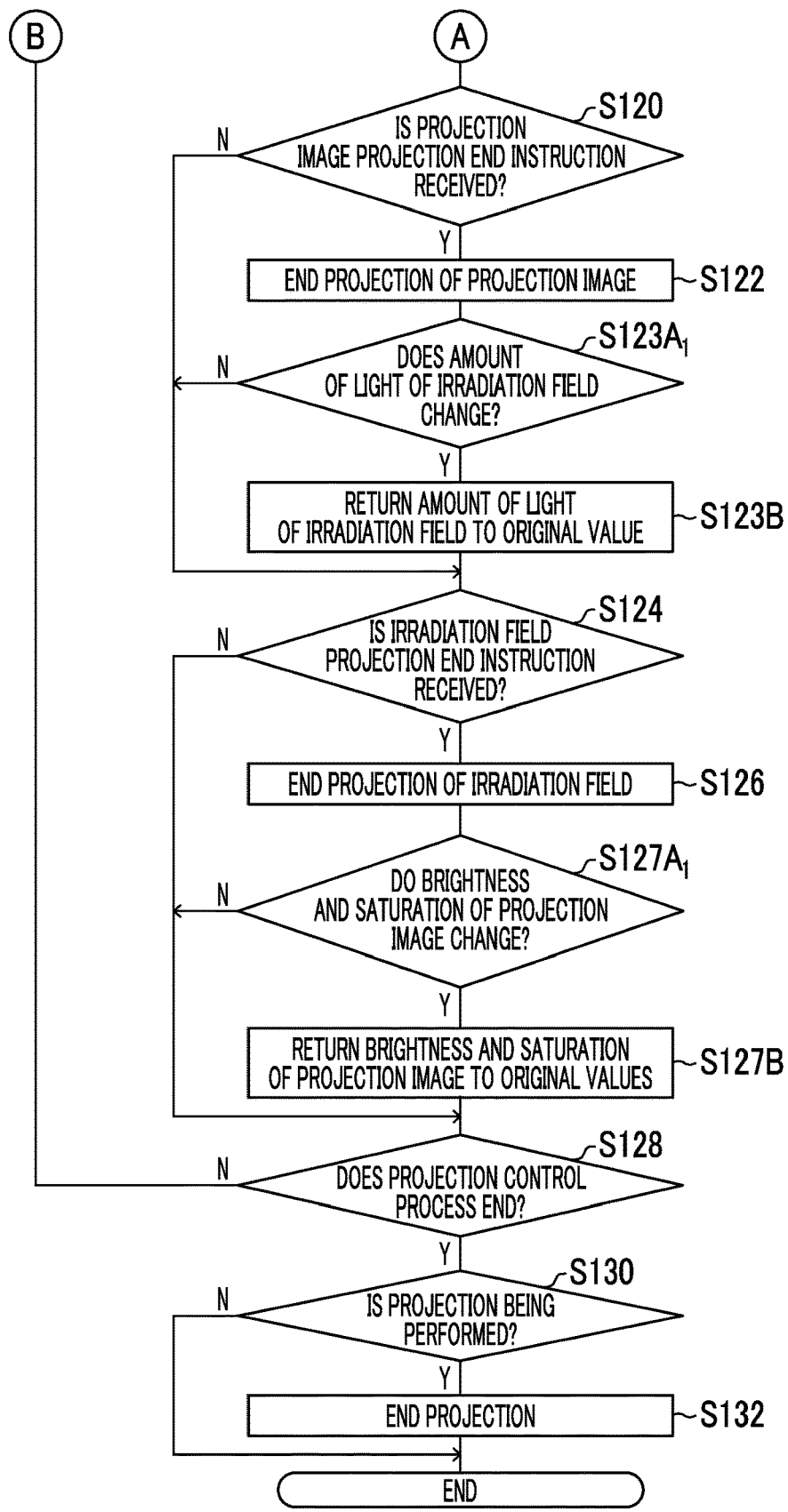

In a case in which both the instruction to start the projection of the projection image P and the instruction to start the projection of the irradiation field 102 are received, both at least one of the brightness or saturation of the projection image P and the amount of light of the irradiation field 102 may be controlled such that projection corresponding to the instruction received later is highlighted. That is, the projection corresponding to the instruction received later may be highlighted by making the projection corresponding to the instruction received first less noticeable than usual and making the projection corresponding to the instruction received later more noticeable than usual. FIGS. 8C and 8D are flowcharts illustrating an example of the projection control process in this case.

The projection control process illustrated in FIGS. 8C and 8D differs from the projection control process illustrated in FIGS. 8A and 8B in that it comprises Steps $S111B_1$, $S119B_1$, $S123A_1$, and $S127A_1$ instead of Steps S111B, S119B, S123A, and S127A, respectively.

In the example illustrated in FIGS. 8C and 8D, in a case in which the determination result in Step S111A is "Yes" since the irradiation field 102 is being projected, the process proceeds to Step $S111B_1$. In Step $S111B_1$, the control unit 62 decreases the amount of light of the irradiation field 102 that is being projected and increases the brightness and saturation of the projection image P whose projection has been started in Step S110. Specifically, the control unit 62 outputs an instruction to decrease the amount of light of the irradiation field 102 and a brightness and saturation increase instruction for increasing the brightness and saturation of the display image displayed according to the projection image P to the mammography apparatus 10 through the I/F unit 54. In the mammography apparatus 10, as described above, in a case in which the light amount decrease instruction is input, the control unit 20 decreases the amount of light of the visible light source 37V to dim the visible light V emitted from the visible light source 37V. Further, in the mammography apparatus 10, in a case in which the brightness and saturation increase instruction is input, the control unit 20 increases the brightness and saturation of the pixels of the projection unit 48B of the projector 48. Here, how much the amount of visible light V is decreased and how much the brightness and saturation of the projection image P are increased are not particularly limited. However, the display image displayed according to the projection image P may be more highlighted (noticeable) than the displayed irradiation field 102. For example, in a case in which the amount of visible light V is decreased to the same extent as the processing result of Step S111B in the projection control process illustrated in FIGS. 8A and 8B, the display image displayed according to the projection image P is more highlighted (noticeable) than the processing result of Step S111B. Further, for example, in a case in which the display image displayed according to the projection image P is highlighted (noticeable) to the same extent as the processing result of Step S111B in the projection control process illustrated in FIGS. 8A and 8B, it is possible to decrease the amount of visible light V to be decreased in Step 111B$_1$.

Further, in the example illustrated in FIGS. 8C and 8D, in a case in which the determination result in Step S119A is "Yes" since the projection image P is being projected, the process proceeds to Step S119B$_1$. In Step S119B$_1$, the control unit 62 decreases the brightness and saturation of the projection image P that is being projected and increases the amount of light of the irradiation field 102 whose projection has been started in Step S118. Specifically, the control unit 62 outputs a brightness and saturation decrease instruction for decreasing the brightness and saturation of the display image displayed according to the projection image P and a light amount increase instruction for increasing the amount of light of the irradiation field 102 to the mammography apparatus 10 through the I/F unit 54. In the mammography apparatus 10, as described above, in a case in which the brightness and saturation decrease instruction is input, the control unit 20 decreases the brightness and saturation of the pixels of the projection unit 48B of the projector 48. Further, in the mammography apparatus 10, in a case in which the light amount increase instruction is input, the control unit 20 increases the amount of light emitted from the visible light source 37V to brighten the visible light V emitted from the visible light source 37V. Here, how much the brightness and saturation of the projection image P are decreased and how much the visible light V is brightened are not particularly limited. However, the displayed irradiation field 102 may be more highlighted (noticeable) than the display image displayed according to the projection image P. For example, in a case in which the brightness and saturation of the projection image P are decreased to the same extent as the processing result of Step S119B in the projection control process illustrated in FIGS. 8A and 8B, the irradiation field 102 is more highlighted (noticeable) than the processing result of Step S119B. Further, for example, in a case in which the irradiation field 102 is highlighted (noticeable) to the same extent as the processing result of Step S119B in the projection control process illustrated in FIGS. 8A and 8B, it is possible to reduce the degree of decrease in the brightness and saturation of the projection image Pin Step 119B$_1$.

Further, in the example illustrated in FIGS. 8C and 8D, after the control unit 62 ends the projection of the projection image P (S122), it determines whether or not the amount of light of the irradiation field 102 has been changed in Step S123A$_1$. Specifically, the control unit 62 determines whether or not the irradiation field 102 is projected in a state in which the amount of visible light V is decreased by the process in Step S111B$_1$ or in a state in which the amount of visible light V is increased by the process in Step S119B$_1$. In a case in which the amount of light of the irradiation field 102 is neither decreasing nor increasing, the determination result in Step S123A$_1$ is "No", and the process proceeds to Step S124. On the other hand, in a case in which the amount of light of the irradiation field 102 is decreasing or increasing, the determination result in Step S123A$_1$ is "Yes", and the process proceeds to Step S123B.

In Step S123B, the control unit 62 returns the amount of light of the irradiation field 102 that is decreasing or increasing to the original value and returns the amount of visible light V that is emitted to project the irradiation field 102 to the amount of light in a case in which the projection image P is not projected.

Further, in the example illustrated in FIGS. 8C and 8D, after the control unit 62 ends the projection of the irradiation field 102 (S126), it determines whether or not the brightness and saturation of the projection image P have been changed in Step S127A$_1$. Specifically, the control unit 62 determines whether or not the projection image P is projected in a state in which the brightness and saturation are increased by the process in Step S111B$_1$ or in a state in which the brightness and saturation are decreased by the process in Step S119B$_1$. In a case in which the brightness and saturation of the projection image P are neither increasing nor decreasing, the determination result in Step S127A$_1$ is "No", and the process proceeds to Step S128. On the other hand, in a case in which the brightness and saturation of the projection image P are increasing or decreasing, the determination result in Step S127A$_1$ is "Yes", and the process proceeds to Step S127B.

In Step S127B, the control unit 62 returns the brightness and saturation of the projection image P that are increasing or decreasing to the brightness and saturation in a case in which the irradiation field 102 is not projected.

Modification Example 2

Figure 8E:
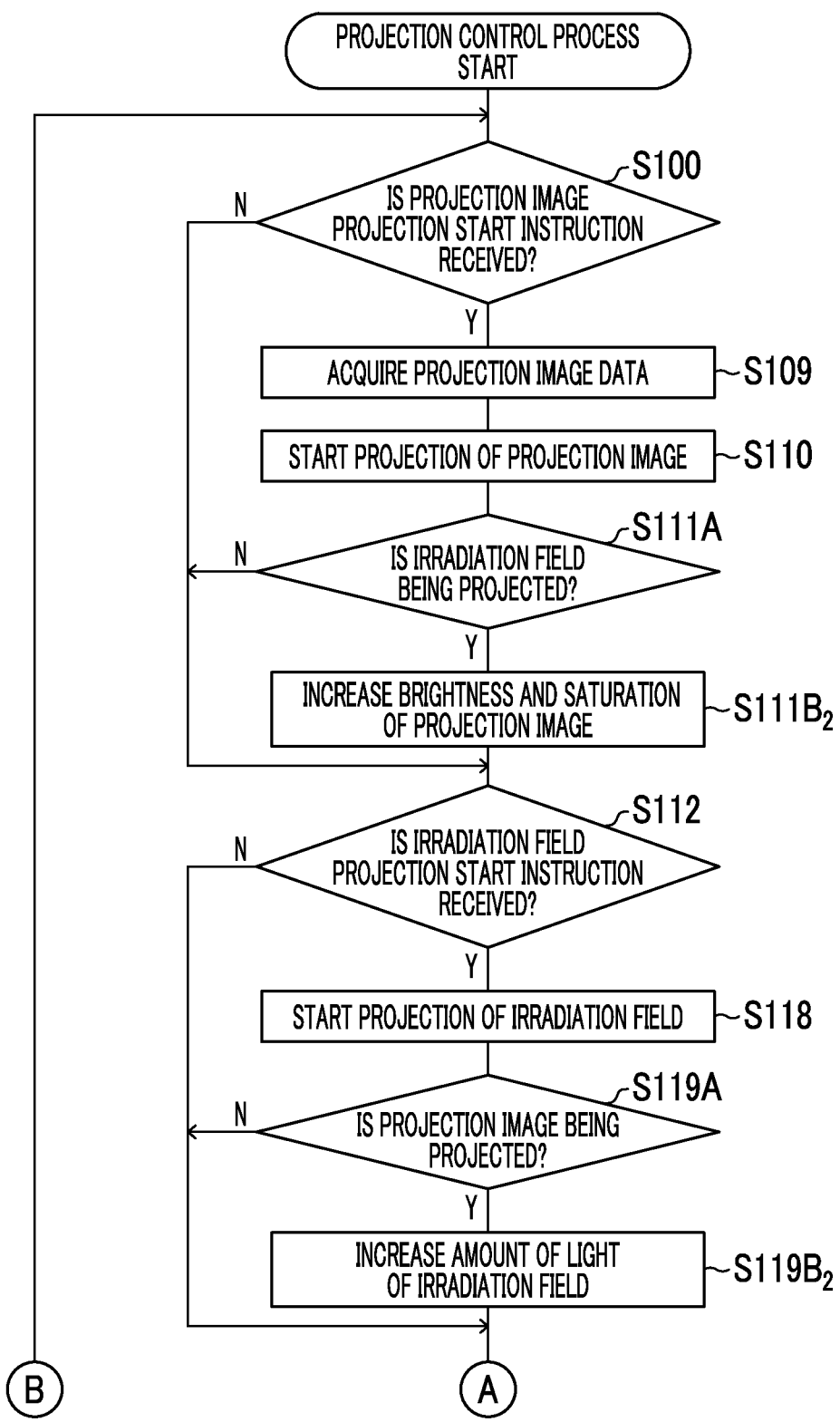
FIGS. 8E and 8F are flowcharts illustrating an example of the flow of a projection control process according to Modification Example 2 of the second embodiment.
Figure 8F:
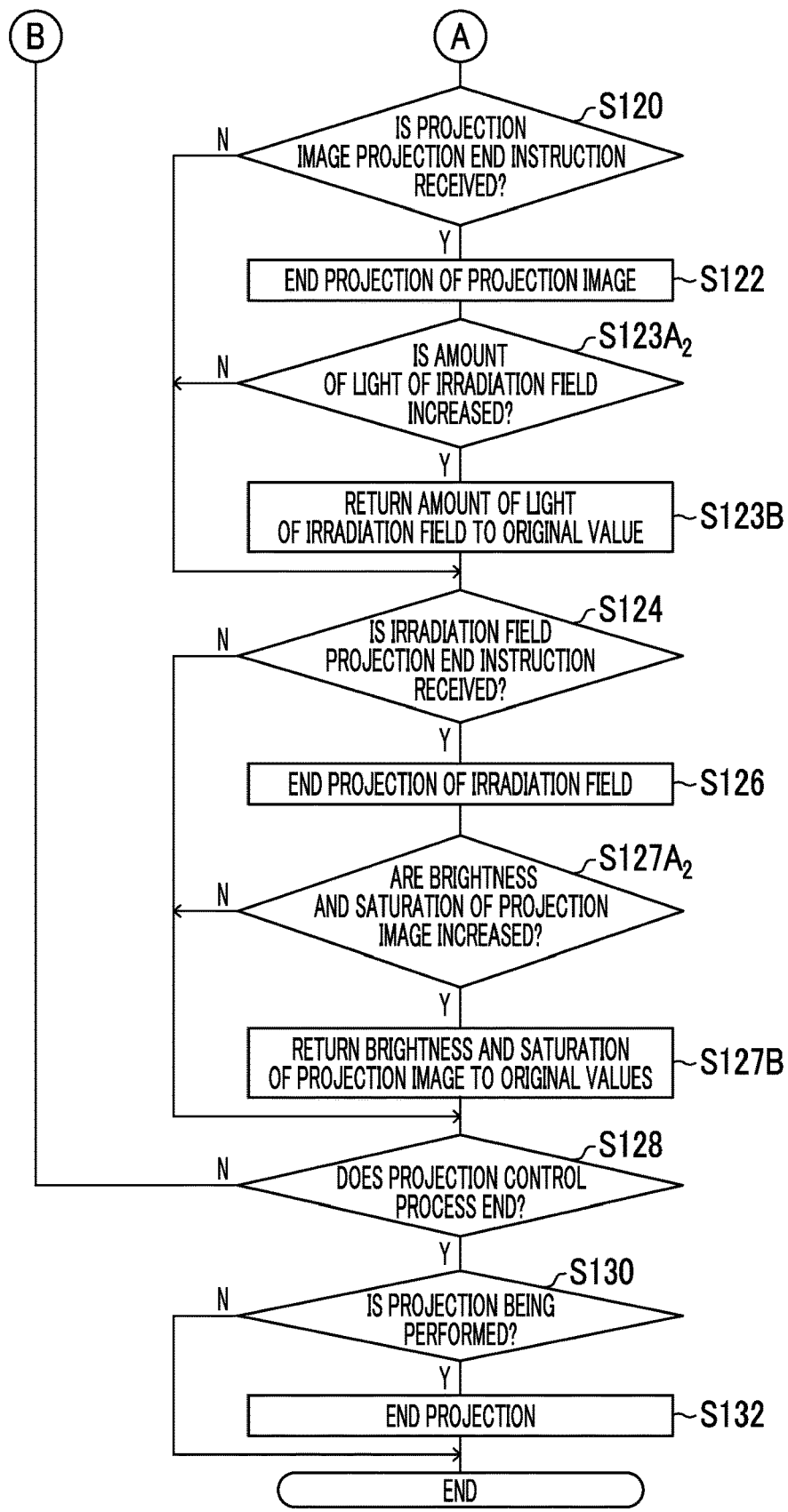

In a case in which both the instruction to start the projection of the projection image P and the instruction to start the projection of the irradiation field 102 are received, both at least one of the brightness or saturation of the projection image P and the amount of light of the irradiation field 102 may be controlled to suppress projection corresponding to the instruction received first. That is, projection corresponding to the instruction received first may be less noticeable than usual to highlight the projection corresponding to the instruction received later. FIGS. 8E and 8F are flowcharts illustrating an example of the projection control process in this case.

The projection control process illustrated in FIGS. 8E and 8F differs from the projection control process illustrated in FIGS. 8A and 8B in that it comprises Steps S111B$_2$, S119B$_2$, S123A$_2$, and S127A$_2$ instead of Steps S111B, S119B, S123A, and S127A, respectively.

In the example illustrated in FIGS. 8E and 8F, in a case in which the determination result in Step S111A is "Yes" since the irradiation field 102 is being projected, the process proceeds to Step S111B$_2$. In Step S111B$_2$, the control unit 62 increases the brightness and saturation of the projection image P whose projection has been started in Step S110. Specifically, the control unit 62 outputs a brightness and saturation increase instruction for increasing the brightness and saturation of the display image displayed according to the projection image P to the mammography apparatus 10 through the I/F unit 54. In the mammography apparatus 10, as described above, in a case in which the brightness and saturation increase instruction is input, the control unit 20 increases the brightness and saturation of the pixels of the projection unit 48B of the projector 48. Here, how much the brightness and saturation of the projection image P are increased is not particularly limited. However, the display image displayed according to the projection image P may be more highlighted (noticeable) than the displayed irradiation field 102.

Further, in the example illustrated in FIGS. 8E and 8F, in a case in which the determination result in Step S119A is "Yes" since the projection image P is being projected, the process proceeds to Step S119B$_2$. In Step S119B$_2$, the control unit 62 increases the amount of light of the irradiation field 102 whose projection has been started in Step S118. Specifically, the control unit 62 outputs a light amount increase instruction for increasing the amount of light of the irradiation field 102 to the mammography apparatus 10 through the I/F unit 54. In the mammography apparatus 10, as described above, in a case in which the light amount increase instruction is input, the control unit 20 increases the amount of light emitted from the visible light source 37V to brighten the visible light V emitted from the visible light source 37V. Here, how much the visible light V is brightened is not particularly limited. However, the displayed irradiation field 102 may be more highlighted (noticeable) than the display image displayed according to the projection image P.

Further, in the example illustrated in FIGS. 8E and 8F, after the control unit 62 ends the projection of the projection image P (S122), it determines whether or not the amount of light of the irradiation field 102 is increasing in Step S123A$_2$. Specifically, the control unit 62 determines whether or not the irradiation field 102 is projected in a state in which the amount of visible light V is increased by the process in Step S119B$_2$. In a case in which the amount of light of the irradiation field 102 is not increasing, the determination result in Step S123A$_2$ is "No", and the process proceeds to Step S124. On the other hand, in a case in which the amount of light of the irradiation field 102 is increasing, the determination result in Step S123A$_2$ is "Yes", and the process proceeds to Step S123B.

In Step S123B, the control unit 62 returns the amount of light of the irradiation field 102 that is increasing to the original value and returns the amount of visible light V emitted in order to project the irradiation field 102 to the amount of light in a case in which the projection image P is not projected.

Further, in the example illustrated in FIGS. 8E and 8F, after the control unit 62 ends the projection of the irradiation field 102 (S126), it determines whether or not the brightness and saturation of the projection image P are increasing in Step S127A$_2$. Specifically, the control unit 62 determines whether or not the projection image P is projected in a state in which the brightness and saturation are increased by the process in Step S111B$_2$. In a case in which the brightness and saturation of the projection image P are not increasing, the determination result in Step S127A$_2$ is "No", and the process proceeds to Step S128. On the other hand, in a case in which the brightness and saturation of the projection image P are increasing, the determination result in Step S127A$_2$ is "Yes", and the process proceeds to Step S127B.

In Step S127B, the control unit 62 returns the brightness and saturation of the projection image P which are increasing to the brightness and saturation in a case in which the irradiation field 102 is not projected.

Third Embodiment

In this embodiment, a difference in the control of each of the projection of the projection image P and the projection of the irradiation field 102 from the first embodiment will be described.

In addition, the configuration of the console 12 according to this embodiment differs from that of the console 12 according to the first embodiment (see FIG. 3) in that the projection image data 53B is not stored in the storage unit 52 of the console 12. Further, since the functions of the control unit 62 included in the console 12 according to this embodiment are different from those of the control unit 62 (see FIG. 4) according to the first embodiment, the functions of the control unit 62 according to this embodiment will be described, and the description of the same configuration will not be repeated.

The control unit 62 according to this embodiment has a function of controlling the mammography apparatus 10 such that the projection image P to be projected is switched between a case in which the range of the irradiation field 102 is displayed and a case in which the range of the irradiation field 102 is not displayed. For example, in a case in which the range of the irradiation field 102 is displayed, the control unit 62 according to this embodiment performs control to project the projection image P for displaying information outside the range of the irradiation field 102.

Figure 9A:
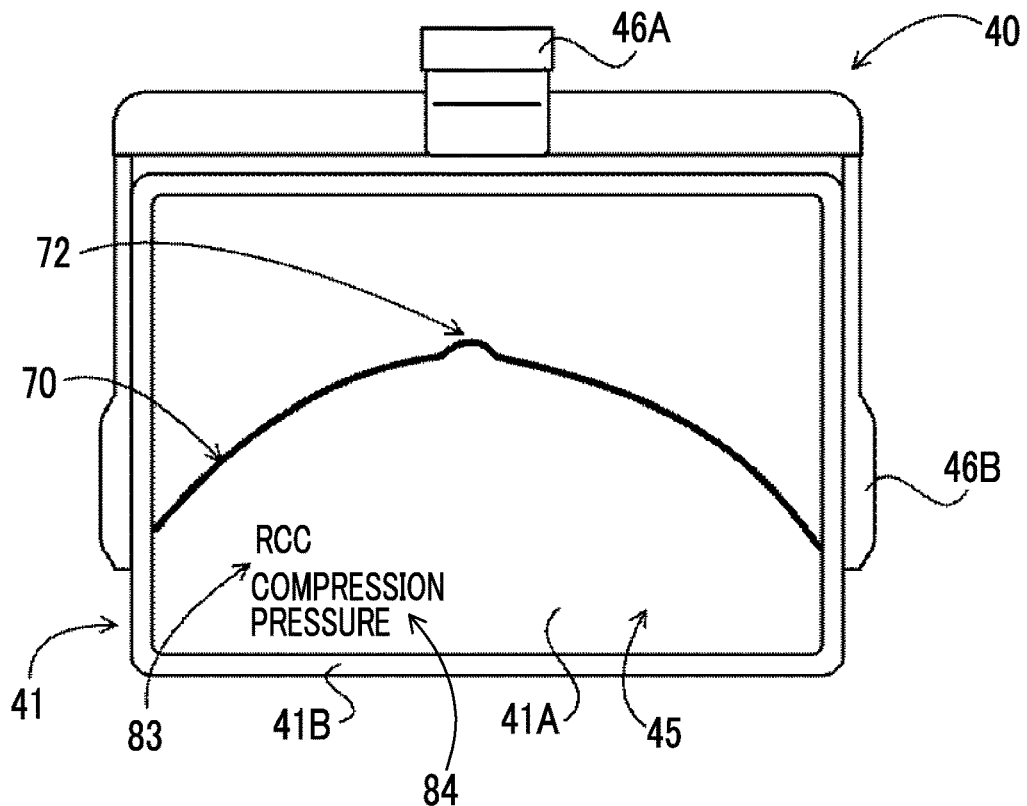
FIG. 9A is a diagram illustrating an example of the skin line, the position of the nipple, and characters displayed on the projection surface of the compression plate according to the projection image in a case in which the irradiation field is not displayed.

For example, FIG. 9A illustrates examples of the skin line 70, the position 72 of the nipple, characters 83 indicating CC imaging (RCC) for the right breast, and characters 84 indicating compression pressure which are displayed on the projection surface 45 of the compression plate 40 according to the projection image P. As described above, in a case in which the irradiation field 102 is projected, the information (image) displayed by the projection image P may not be visible due to the visible light V. In FIG. 9A, for convenience, "compression pressure" is described as an example of the characters 84. However, for example, at least one of the current compression pressure of the compression plate 40 against the breast or the compression pressure in a case in which compression was completed in a past imaging is actually displayed.

In a case in which the irradiation field 102 is displayed as illustrated in FIG. 6C in a state in which the display of the state illustrated in FIG. 9A is performed by the projection image P, it is difficult or impossible to visually recognize the information of a region corresponding to the irradiation field 102. Specifically, it is difficult or impossible to visually recognize the information of a portion of the skin line 70 that becomes the irradiation field 102, the position 72 of the nipple, the characters 83, and the characters 84.

Figure 9B:
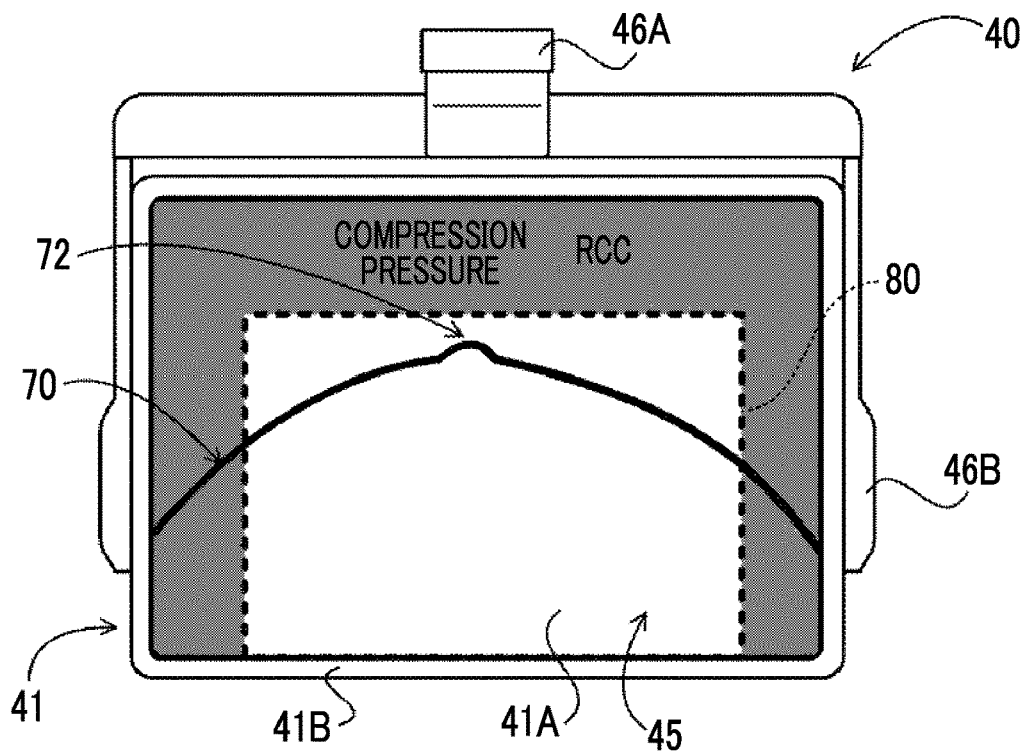
FIG. 9B is a diagram illustrating an example of the skin line, the position of the nipple, and the characters displayed on the projection surface of the compression plate according to the projection image in a case in which the irradiation field is displayed.

Therefore, the control unit 62 according to this embodiment projects the projection image P in which information is also displayed in a region inside the irradiation field 102 in a case in which the range of the irradiation field 102 is not displayed and projects the projection image P for displaying information outside the region inside the irradiation field 102 in a case in which the range of the irradiation field 102 is displayed. For example, in a case in which the range of the irradiation field 102 is not displayed, the control unit 62 projects the projection image P by which the state illustrated in FIG. 9A is displayed. Then, in a case in which the range of the irradiation field 102 is displayed, the control unit 62 projects the projection image P by which the state illustrated in FIG. 9B is displayed. In the example illustrated in FIG. 9B, the aspect in which the characters 83 and 84 are displayed outside the irradiation field 102 is illustrated. On the other hand, the breast is positioned in the same manner as described above, regardless of whether or not the range of the irradiation field 102 is displayed. Therefore, the display positions of the skin line 70 and the position 72 of the nipple do not change regardless of whether or not the range of the irradiation field 102 is displayed.

In addition, in this embodiment, instead of the projection image data 53 stored in the storage unit 52 in the first embodiment, projection image data 53 indicating the projection image P for displaying information outside the range of the irradiation field 102, which is illustrated in FIG. 9B, is stored.

Figure 10A:
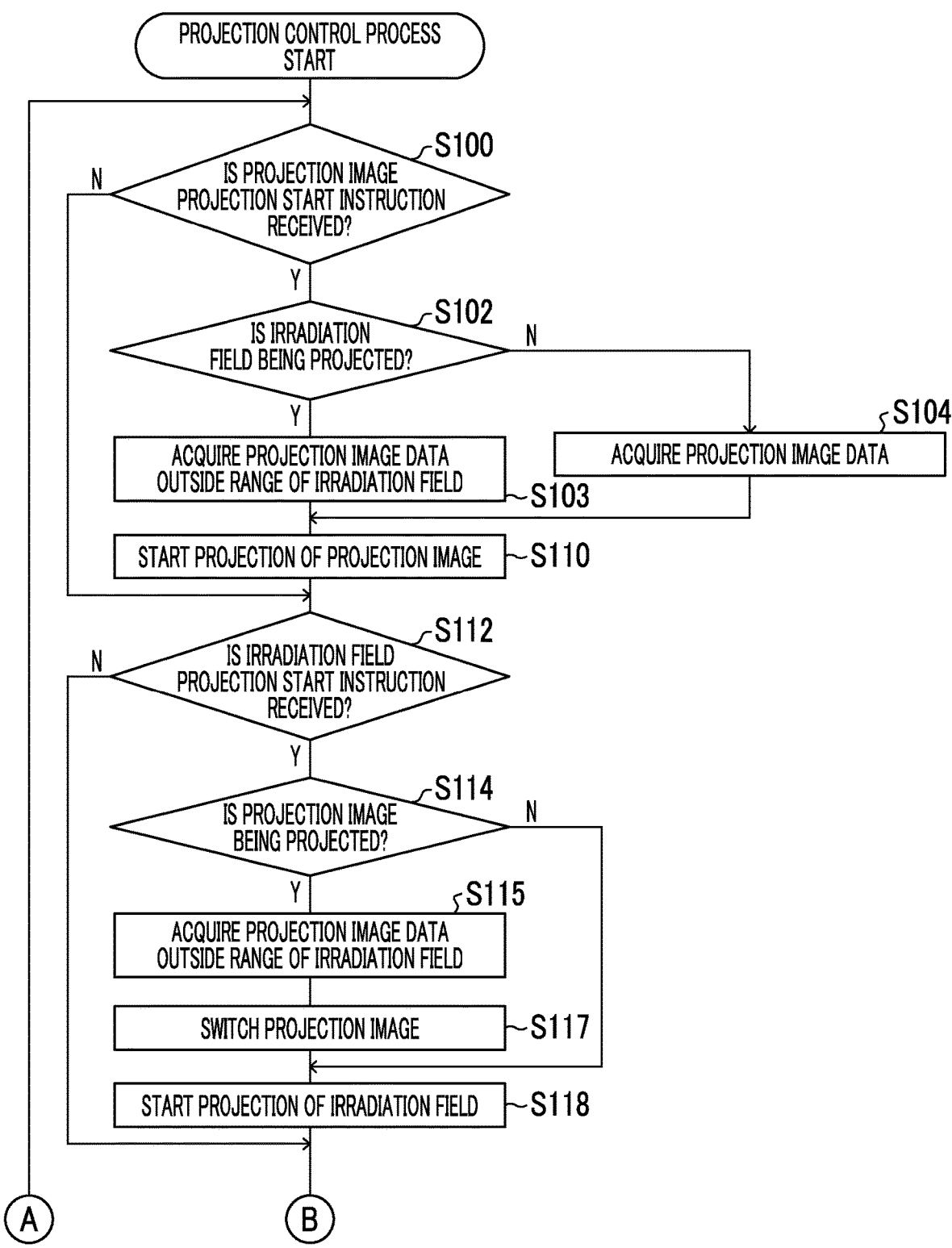
FIGS. 10A and 10B are flowcharts illustrating an example of the flow of a projection control process according to a third embodiment.
Figure 10B:
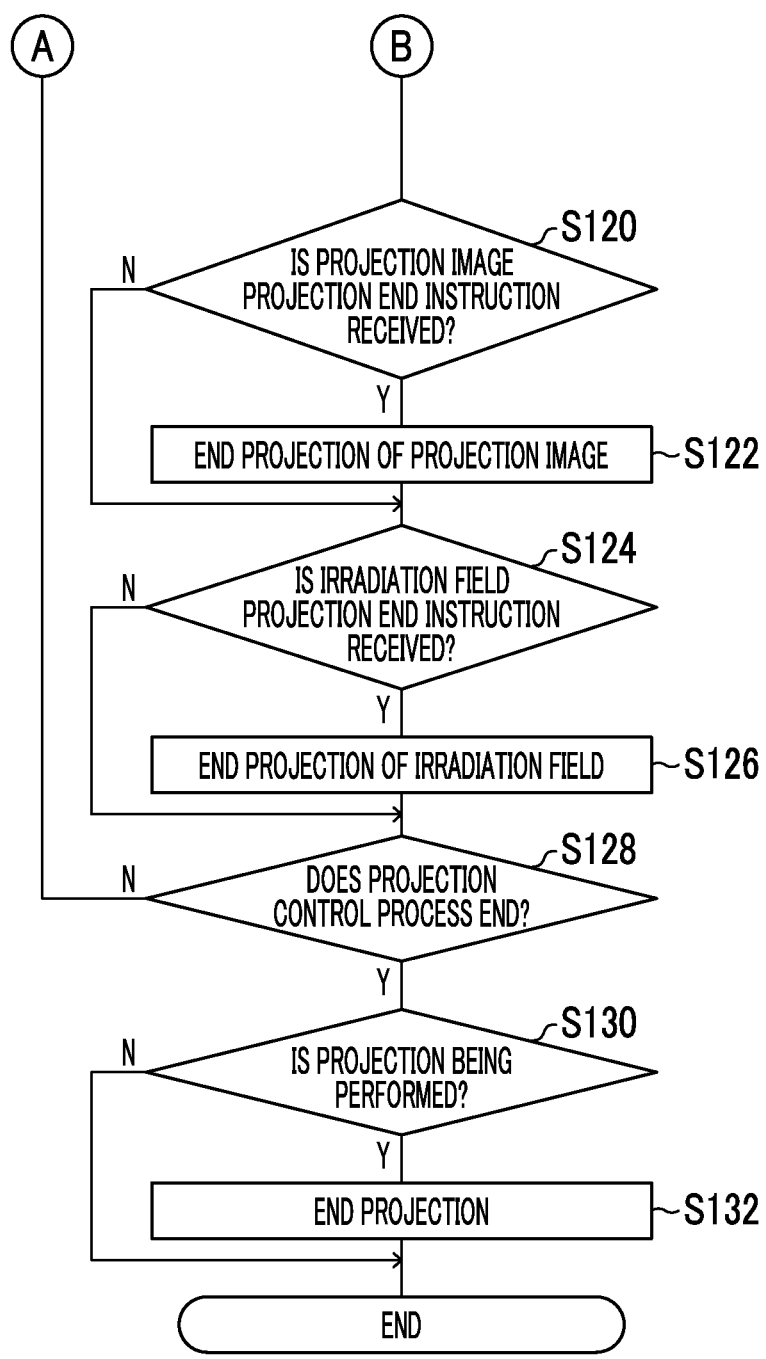

Further, since a projection control process performed in the console 12 in this embodiment differs from that in the first embodiment, the projection control process according to this embodiment will be described. FIGS. 10A and 10B are flowcharts illustrating an example of the flow of the projection control process performed in the console 12 according to this embodiment.

As illustrated in FIGS. 10A and 10B, the projection control process according to this embodiment differs from the projection control process (see FIGS. 5A and 5B) according to the first embodiment in that it comprises a process in Step S103 instead of the processes in Steps S106 and S108 and comprises processes in Steps S115 and S117 instead of Step S116.

In this embodiment, in a case in which the instruction to start the projection of the projection image P is received while the irradiation field 102 is being projected, the process proceeds to Step S103 as illustrated in FIGS. 10A and 10B. In Step S103, the control unit 62 acquires the projection image data 53 for displaying information outside the range of the irradiation field 102 from the storage unit 52.

Further, in a case in which the instruction to start the projection of the irradiation field 102 is received while the projection image P is being projected, the process proceeds to Step S115 as illustrated in FIGS. 10A and 10B. In Step S115, the control unit 62 acquires the projection image data 53 for displaying information outside the range of the irradiation field 102 from the storage unit 52 as in Step S103.

Then, in Step S117, the control unit 62 switches the projection image P that is currently projected from the projection image P that is currently being projected to the projection image P corresponding to the projection image data 53 acquired in Step S115. With this process, information is displayed in the state illustrated in FIG. 9B by the switched projection image P.

As described above, in the console 12 according to this embodiment, in a case in which the projection image P to be projected is switched to display the irradiation field 102, information can be displayed outside the range of the irradiation field 102 by the projection image P. Therefore, according to the console 12 of this embodiment, it is possible to prevent the projection image P and the range of the irradiation field 102 from being unrecognizable.

In addition, in this embodiment, the aspect in which the control unit 62 performs control to project the projection image P for displaying information outside the range of the irradiation field 102 in a case in which the range of the irradiation field 102 is displayed has been described. However, the present disclosure is not limited to this aspect and may be applied to any aspect as long as information is displayed outside the irradiation field 102 by the projection image P. For example, in a case in which the irradiation field 102 is displayed on the projection surface 45 of the compression plate 40, information may be displayed on the wall portion 41B of the compression plate 40 by the projection image P. In this case, instead of switching the projection image P to be projected, the emission direction or position of the projection light by the projector 48 may be adjusted to display information outside the irradiation field 102 using the projection image P.

As described above, according to the console 12 of each of the above-mentioned aspects, in the mammography apparatus 10 that emits the projection light in order to project the projection image P and that emits the visible light V in order to project the irradiation field 102, it is possible to prevent the projection image P and the range of the irradiation field 102 from being unrecognizable.

In addition, in the first embodiment, in a case in which the instruction to start the projection of the projection image P is received while the irradiation field 102 is being projected, the projection of the projection image P is ended even though the instruction to end the projection of the projection image P is not received. Further, in a case in which the instruction to start the projection of the irradiation field 102 is received while the projection image P is being projected, the projection of the irradiation field 102 is ended even though the instruction to end the projection of the irradiation field 102 is not received. However, in a case in which the instructions to end the projection of the projection image P and the irradiation field 102 are not received, after the projection of one of the projection image P and the irradiation field 102 is ended, the projection of the other of the projection image P and the irradiation field 102 may be started. Specifically, in a case in which the instruction to end the projection of the irradiation field 102 is received after the projection of the projection image P is ended and the projection of the irradiation field 102 is started by the reception of the instruction to start the projection of the irradiation field 102, the projection of the irradiation field 102 may be ended, and the projection image P may be projected again. Further, in a case in which the instruction to end the projection of the projection image P is received after the projection of the irradiation field 102 is ended and the projection of the projection image P is started by the reception of the instruction to start the projection of the projection image P, the projection of the projection image P may be ended, and the irradiation field 102 may be projected again.

Further, the present disclosure is not limited to each of the above-described embodiments. For example, priority may be given to one of the projection image P and the irradiation field 102, and the projection of the projection image P or the irradiation field 102 having priority may not be automatically ended. For example, in a case in which priority is given to the projection image P, the processes in Steps S100 to S110 of the projection control process (see FIGS. 5A and 5B) according to the first embodiment and the processes in Steps S112 to S119B of the projection control process (see FIGS. 8A and 8B) according to the second embodiment may be combined with each other.

Further, in each of the above-described embodiments, the aspect in which each of the projection image P and the irradiation field 102 is projected in response to the instruction from the user has been described. However, the timing when the projection of each of the projection image P and the irradiation field 102 is started is not limited to this aspect. For example, in a case in which the compression plate 40 is moved in the compression direction, the projection of the projection image P may be automatically started.

In a case in which the console 12 automatically starts the projection of each of the projection image P and the irradiation field 102 and automatically ends the projection after a few seconds regardless of the instruction from the user, the control according to each of the above-described embodiments may not be performed. For example, no control may be performed for the projection image P in the following case: the console 12 automatically starts the projection of the irradiation field 102 in a case in which the compression plate 40 is moved in the compression direction or in a case in which the compression pressure of the compression plate 40 against the breast is equal to or greater than a threshold value and automatically ends the projection after a few seconds. In other words, control to continuously project the projection image P in the same state may be performed. In this way, in a case in which projection is ended after a few seconds, the projection is immediately returned to the original state. Therefore, the control according to each of the above-described embodiments may not be performed.

Further, in each of the above-described embodiments, the aspect in which both the size of the projection image P and the size of the irradiation field 102 are equal to or less than the size of the projection surface 45 has been described. However, the size of the projection image P and the size of the irradiation field 102 may be equal to or greater than the size of the projection surface 45 of the compression plate 40. That is, at least one of the projection image P or the irradiation field 102 may be projected onto the imaging surface 30A of the imaging table 30. Further, for example, the projection image P may be displayed on the wall portion 41B of the compression plate 40. Furthermore, the projection image P may be projected only on the imaging table 30. The irradiation field 102 is projected onto the projection surface 45 of the compression plate 40. Therefore, even in a case in which the projection image P and the irradiation field 102 are projected at different positions, both are projected at near positions. Therefore, projection corresponding to the projection start instruction received later is highlighted as in each of the above-described embodiments to prevent the projection image P and the range of the irradiation field 102 from being unrecognizable.

Further, in each of the above-described embodiments, the aspect in which the irradiation field 102 is displayed by the projection image P using the projection image data 53B including the image for displaying the irradiation field 102 has been described. However, a specific method for displaying the irradiation field 102 using the projection image P is not limited to this aspect. For example, a projection image P obtained by superimposing an image indicating the irradiation field 102 on the projection image based on the projection image data 53A may be projected.

Further, the configuration for projecting the projection image P in the mammography apparatus 10 described in each of the above-described embodiments is not limited and is not limited to the aspect using the projector 48. Further, in a case in which the projector 48 is applied, the configuration of the projector 48 is not limited. For example, in each of the above-described embodiments, the aspect in which the projection image P projected from the projector 48 is directly projected onto the projection surface 45 has been described. However, the projection image P may be reflected from a mirror or the like to be projected onto the projection surface 45. In this case, the direction in which the projection image P is projected can be adjusted by the mirror or the like. Furthermore, for example, a shutter or the like that blocks the projection light may be provided in front of the projection unit 48B of the projector 48. In this case, the shutter may be opened or closed to control the projection of the projection image P onto the projection surface 45. Specifically, in a case in which the projection of the projection image P is started, control is performed such that the shutter is opened to transmit the projection light. On the other hand, in a case in which the projection of the projection image P is ended, control is performed such that the shutter is closed to block the projection light.

Further, the projection image P is not limited to the projection image for displaying the image for guiding at least one of the shape or position of the breast on the projection surface 45 of the compression plate 40 and may be a projection image P for displaying character information as illustrated in FIGS. 9A and 9B. For example, the projection image P may be a projection image for displaying information related to the subject, such as the name of the subject, and information related to compression, such as compression pressure or the height of the compression plate 40, on the projection surface 45 of the compression plate 40. In addition, the projection image P may be a projection image for displaying a plurality of information items. Furthermore, the projection image P may be, for example, information related to the current imaging, such as an imaging date and time or a radiographer, information related to a past imaging, such as compression pressure in the past imaging, information related to the subject, such as the name of the subject, and information related to the radiographer, or may be an image indicating characters or numbers.

Further, in each of the above-described embodiments, the image indicating the skin line of the breast and the position of the nipple in a case in which a standard breast is compressed into an ideal state is applied as the projection image P. However, the projection image P is not limited to this aspect. For example, the projection image P may be the radiographic image of the breast of the same subject captured in the past, an image indicating a skin line generated from the radiographic image captured in the past, or the like. In addition, a method for generating the image indicating the skin line is not particularly limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line. In addition, for example, JP2010-051456A discloses a method which divides a radiographic image of the breast into a breast region and a blank region on the basis of the density of each pixel of the radiographic image and connects the pixels which are the boundary points between the breast region and the blank region to generate a skin line.

Further, in a case in which the image indicating the skin line or the position of the nipple is generated from the radiographic image captured in the past and is projected onto the projection surface 45 and the projection image P generated from the radiographic image captured in the past is projected without any change, the size of the projection image P may be different from the size of the projection surface 45.

In a case in which the radiographic image captured in the past is larger than the projection surface 45, the control unit 62 may generate a guide projection image P indicating the skin line based on the shape of the breast indicated by a partial region of the radiographic image which corresponds to the size of the projection surface 45. In other words, the control unit 62 may cut a partial region corresponding to the size of the projection surface 45 in the radiographic image captured in the past and may generate the projection image P indicating the skin line or the position of the nipple on the basis of the cut image. In addition, in many cases, the mammography apparatus 10 captures an image including a chest wall side. Therefore, the region to be cut is preferably a partial region on the chest wall side. Further, it is preferable that the region to be cut is a partial region including the center of the shape of the breast included in the radiographic image in a left-right direction.

Furthermore, in a case in which the radiographic image captured in the past is smaller than the projection surface 45, the control unit 62 may generate a projection image P which indicates a skin line and the position of the nipple and in which the shape of the breast outside the radiographic image has been complemented on the basis of the shape of the breast indicated by the radiographic image. A known image complementing method can be applied as the complementing method. For example, the control unit 62 may complement an extension line on the basis of the curvature of the skin line of a portion generated on the basis of the radiographic image captured in the past. Further, for example, the control unit 62 may complement a tangent line of the skin line of the portion generated on the basis of the radiographic image as the extension line.

Further, in a case in which the size of the radiographic image captured in the past and the size of the projection surface 45 are not matched with each other, the control unit 62 may generate a projection image P indicating the skin line or the position of the nipple based on the shape of the breast indicated by an image obtained by enlarging or reducing the radiographic image captured in the past according to the size of the projection surface 45. For example, an enlargement and reduction ratio may be predetermined for each combination of the size of the radiographic image and the size of the projection surface 45.

Further, in each of the above-described embodiments, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the receiving unit 60 and the control unit 62.

Further, in each of the above-described embodiments, for example, the following various processors can be used as the hardware structure of processing units performing various processes such as the receiving unit 60 and the control unit 62. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the projection control program 51 is stored (installed) in the ROM 50B in advance has been described. However, the present disclosure is not limited thereto. The projection control program 51 may be recorded on a recording medium, such as a compact disc read only memory (CD-ROM), a digital versatile disc read only memory (DVD-ROM), or a universal serial bus (USB) memory, and then provided. In addition, the projection control program 51 may be downloaded from an external device through a network.

What is claimed is:

1. A control device comprising:
   at least one processor,
   wherein the processor is configured to
   control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field do not occur simultaneously, and
   perform the above control in a case in which an instruction to start the projection of the range of the irradiation field is received while the projection image is being projected.

2. The control device according to claim 1,
   wherein the processor is configured to perform the control in a case in which an instruction to end the projection of the range of the irradiation field is received.

3. The control device according to claim 1,
   wherein the projection image includes an indication of the range of the irradiation field.

4. The control device according to claim 3,
   wherein the indication of the range of the irradiation field includes making at least one of brightness or saturation of a region of the projection image within the range of the irradiation field different from the at least one of the brightness or the saturation of a region outside the range of the irradiation field.

5. The control device according to claim 3,
   wherein the indication of the range of the irradiation field includes a line or a mark indicating a boundary between an inside and an outside of the irradiation field.

6. The control device according to claim 1,
   wherein, in a case in which an instruction to start the projection of the projection image and an instruction to start the projection of the range of the irradiation field are received, instead of the control, the processor is configured to perform control to project both the range of the irradiation field and a projection image of which at least one of brightness or saturation is lower than that in a case in which only the projection image is projected.

7. The control device according to claim 1,
   wherein, in a case in which an instruction to start the projection of the projection image and an instruction to start the projection of the range of the irradiation field are received, instead of the control, the processor is configured to perform control to project both the projection image and a range of the irradiation field in which the visible light is dimmer than that in a case in which the range of the irradiation field is projected by the reception of only the instruction to start the projection of the range of the irradiation field of the instructions.

8. A control device comprising:
at least one processor,
wherein the processor is configured to
control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that, in a case in which one of projection of the projection image or projection of the range of the irradiation field is performed and an instruction to start the other projection is received, the projection image or the range of the irradiation field corresponding to the other projection is displayed to be more highlighted than the projection image or the range of the irradiation field corresponding to the one projection, while the projection of the one projection is continued.

9. The control device according to claim 8,
wherein, in a case in which the one projection is the projection of the projection image, the processor is configured to decrease at least one of brightness or saturation of the projection image as the control.

10. The control device according to claim 8,
wherein, in a case in which the one projection is the projection of the projection image, the processor is configured to brighten the visible light as the control.

11. The control device according to claim 8,
wherein, in a case in which the one projection is the projection of the range of the irradiation field, the processor is configured to dim the visible light as the control.

12. The control device according to claim 8,
wherein, in a case in which the one projection is the projection of the range of the irradiation field, the processor is configured to increase at least one of brightness or saturation of the projection image as the control.

13. A control device comprising:
at least one processor,
wherein the processor is configured to
control an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that the projection image to be projected is altered between a case in which the range of the irradiation field is displayed by the irradiation field projection unit and a case in which the range of the irradiation field is not displayed by the irradiation field projection unit.

14. The control device according to claim 13,
wherein, in a case in which the range of the irradiation field is displayed by the irradiation field projection unit, the processor is configured to perform control to display a projection image in which information contained in the projection image is displayed at a region outside the range of the irradiation field, or control to display the projection image at a projection position such that information contained in the projection image is displayed outside the range of the irradiation field.

15. A control method comprising:
controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field do not occur simultaneously, and
performing the above control in a case in which an instruction to start the projection of the range of the irradiation field is received while the projection image is being projected.

16. A control method comprising:
controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that, in a case in which one of projection of the projection image or projection of the range of the irradiation field is performed and an instruction to start the other projection is received, the projection image or the range of the irradiation field corresponding to the other projection is displayed to be more highlighted than the projection image or the range of the irradiation field corresponding to the one projection, while the projection of the one projection is continued.

17. A control method comprising:
controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that the projection image to be projected is altered between a case in which the range of the irradiation field is displayed by the irradiation field projection unit and a case in which the range of the irradiation field is not displayed by the irradiation field projection unit.

18. A non-transitory computer-readable storage medium storing a control program that causes a computer to perform a process comprising:
controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that projection of the projection image and projection of the range of the irradiation field do not occur simultaneously, and performing the above control in a case in which an instruction to start the projection of the range of the irradiation field is received while the projection image is being projected.

19. A non-transitory computer-readable storage medium storing a control program that causes a computer to perform a process comprising:

controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that, in a case in which one of projection of the projection image or projection of the range of the irradiation field is performed and an instruction to start the other projection is received, the projection image or the range of the irradiation field corresponding to the other projection is displayed to be more highlighted than the projection image or the range of the irradiation field corresponding to the one projection, while the projection of the one projection is continued.

20. A non-transitory computer-readable storage medium storing a control program that causes a computer to perform a process comprising:

controlling an image projection unit which projects a projection image onto a projection surface of a compression member and an irradiation field projection unit which projects a range of an irradiation field of radiation using visible light in a mammography apparatus which irradiates a breast compressed by the compression member with the radiation to capture a radiographic image such that the projection image to be projected is altered between a case in which the range of the irradiation field is displayed by the irradiation field projection unit and a case in which the range of the irradiation field is not displayed by the irradiation field projection unit.

* * * * *